US008673582B2

(12) United States Patent
Cuckle et al.

(10) Patent No.: US 8,673,582 B2
(45) Date of Patent: Mar. 18, 2014

(54) METHODS FOR DETERMINING THE RISK OF PRENATAL COMPLICATIONS

(71) Applicants: Wallac Oy, Turku (FI); The Fetal Medicine Foundation, London (GB)

(72) Inventors: Howard Cuckle, Harrogate (GB); Kypros Nicolaides, London (GB)

(73) Assignees: Wallac Oy, Turku (FI); The Fetal Medicine Foundation, London (GB)

( * ) Notice: Subject to any disclaimer, the term of this patent is extended or adjusted under 35 U.S.C. 154(b) by 0 days.

(21) Appl. No.: 13/945,143

(22) Filed: Jul. 18, 2013

(65) Prior Publication Data

US 2013/0344503 A1 Dec. 26, 2013

Related U.S. Application Data

(62) Division of application No. 12/864,625, filed as application No. PCT/US2009/032062 on Jan. 26, 2009, now Pat. No. 8,647,832.

(60) Provisional application No. 61/023,776, filed on Jan. 25, 2008, provisional application No. 61/025,890, filed on Feb. 4, 2008, provisional application No. 61/060,048, filed on Jun. 9, 2008, provisional application No. 61/060,732, filed on Jun. 11, 2008.

(51) Int. Cl.
*G01N 33/53* (2006.01)
*G01N 31/00* (2006.01)

(52) U.S. Cl.
USPC ........ 435/7.21; 435/7.1; 435/287.9; 436/501; 436/518; 427/287; 427/337; 427/338; 530/300; 530/350

(58) Field of Classification Search
None
See application file for complete search history.

(56) References Cited

U.S. PATENT DOCUMENTS

| | | | |
|---|---|---|---|
| 6,735,529 | B1 | 5/2004 | Wald et al. |
| 2004/0038305 | A1 | 2/2004 | Poston et al. |
| 2005/0255114 | A1 | 11/2005 | Labat et al. |
| 2006/0094039 | A1 | 5/2006 | Rosenfeld et al. |
| 2007/0148631 | A1 | 6/2007 | Wright |
| 2007/0178530 | A1 | 8/2007 | Poston et al. |
| 2009/0011429 | A1 | 1/2009 | Poston et al. |

FOREIGN PATENT DOCUMENTS

| | | |
|---|---|---|
| WO | WO 02/37120 | 5/2002 |
| WO | WO 2007/083099 | 7/2007 |

OTHER PUBLICATIONS

Nicolaides et al., "A novel approach to first-trimester screening for early pre-eclampsia combining serum PP-13 and Doppler ultrasound", Ultrasound Obstet Gynecol 27:13-17 (2006).

Papageorghiou et al., "Assessment of risk for the development of pre-eclampsia by maternal characteristics and uterine artery Doppler", BJOG: an International Journal of Obstetrics and Gynaecology 112:703-709 (2005).
Poon et al., "Mean Arterial Pressure at $11^{+0}$ to $13^{+6}$ Weeks in the Prediction of Preeclampsia", Hypertension, Part II, pp. 1027-1033 (2008).
Chinese Office Action, Application No. 200980110513.5; issued Aug. 16, 2013; Applicant: PerkinElmer Health Sciences, Inc.; Wallac Oy; The Fetal Medicine Foundation; Nicolaides Kypros; 5 pages.
European Office Action; Application No. 09704269.1-1405; mailed Apr. 8, 2013; Applicant: PerkinElmer Health Sciences, Inc.; 5 pages.
European Examination Report; Application No. 09704269.1-1223; mailed Feb. 8, 2012 (5 pages).
European Examination Report; Application No. 09704269.1-1223; mailed May 9, 2011 (15 pages).
Akolekar et al., "Maternal serum placental growth factor at 11 + 0 to 13 + 6 weeks of gestation in the prediction of pre-eclampsia," Ultrasound Obstet. Gynecol., 32:732-739 (2008).
Bersinger et al., "Pre-eclampsia: increased, unchanged, and decreased serum markers in comparison to healthy third trimester pregnancy. A synopsis," Immuno-analyse et biologie spécialisée, 20:353-359 (2005).
Bersinger et al., "Pregnancy-associated and placental proteins in the placental tissue of normal pregnant women and patients with pre-eclampsia at term," Eur. J. Endocrinol., 147:785-793 (2002).
Bersinger et al., "Second- and third-trimester serum levels of placental proteins in preeclampsia and small-for-gestational age pregnancies," Acta Obstet. Gynecol. Scand., 83:37-45 (2004).
Bersinger et al., "Second-trimester serum levels of placenta growth factor (PLGF) an inhibin A are increased in smokers. Implications for pre-eclampsia risk assessment," Immuno-analyse et biologie spécialisée, 22:19-23 (2007).
Cuckle et al., "Estimating a woman's risk of having a pregnancy associated with Down's syndrome using her age and serum alpha-fetoprotein level," Br. J. Obstet. Gynaecol., 94:387-402 (1987).
Davey et al., "The classification and definition of the hypertensive disorders of pregnancy," Am. J. Obstet. Gynecol., 158:892-898 (1988).
Debieve et al., "Vascular endothelial growth factor and placenta growth factor concentrations in Down's syndrome and control pregnancies," Mol. Hum. Reprod., 7:765-770 (2001).
GENBANK accession No. AAH78657, 2004.
GENBANK accession No. NM_000737, 2007.
GENBANK accession No. NP_037400, 2011.
GENBANK accession No. P49763, 2001.
International Preliminary Report on Patentability for PCT/US2009/032062, Mailed on Apr. 10, 2009.
International Search Report for International application No. PCT/US 09/32062, Mailed on Apr. 10, 2009.
Kagan et al., "First-trimester screening for trisomy 21 by free beta-human chorionic gonadotropin and pregnancy-associated plasma protein-A: impact of maternal and pregnancy characteristics," Ultrasound Obstet. Gynecol., 31:493-502 (2008).

(Continued)

*Primary Examiner* — Lisa Cook
(74) *Attorney, Agent, or Firm* — Fish & Richardson P.C.

(57) ABSTRACT

The disclosure relates to methods, medical profiles, kits and apparatus for use in determining the risk that a pregnant individual has for developing pre-eclampsia based on amounts of certain biochemical markers in a biological sample from the individual and biophysical markers. The disclosure also relates to methods, medical profiles, kits and apparatus for use in determining the risk that a pregnant individual is carrying a fetus having a chromosomal abnormality based on amounts of certain biochemical markers in a biological sample from the individual and biophysical markers.

16 Claims, 9 Drawing Sheets

(56) References Cited

OTHER PUBLICATIONS

Kagan et al., "Screening for trisomy 21 by maternal age, fetal nuchal translucency thickness, free beta-human chorionic gonadotropin and pregnancy-associated plasma protein-A," Ultrasound Obstet. Gynecol., 31:618-624 (2008).

Khaw et al., "Maternal cardiac function and uterine artery Doppler at 11-14 weeks in the prediction of pre-eclampsia in nulliparous women," BJOG, 115:369-376 (2008).

Konijnenberg et al., "Can flow cytometric detection of platelet activation early in pregnancy predict the occurrence of preeclampsia? A prospective study." American Journal of Obstetrics & Gynecology, vol. 177, No. 2, pp. 434-442, Aug. 1, 1997.

Lambert-Messerlian et al., "Placenta growth factor levels in second-trimester maternal serum in Down syndrome pregnancy and in the prediction of preeclampsia," Prenat. Diagn., 24:876-880 (2004).

Nørgaard-Pedersen et al., "Maternal serum markers in screening for Down syndrome," Clin. Genet., 37:35-43 (1990).

Ødegard et al., "Risk factors and clinical manifestations of pre-eclampsia," BJOG, 107:1410-16 (2000).

Palomaki and Haddow, "Maternal serum alpha-fetoprotein, age, and Down syndrome risk," Am. J. Obstet. Gynecol., 156:460-463 (1987).

Plasencia et al., "Uterine artery Doppler at 11 + 0 to 13 + 6 weeks in the prediction of pre-eclampsia," Ultrasound Obstet. Gynecol., 30:742-749 (2007).

Poon et al., "First-trimester prediction of hypertensive disorders in pregnancy," Hypertension, 53:812-818 (2009).

Poon et al., "Hypertensive disorders in pregnancy: screening by biophysical and biochemical markers at 11-13 weeks," Ultrasound Obstet. Gynecol., 35:662-670 (2010).

Poon et al., "Maternal serum ADAM12 (A disintegrin and metalloprotease) in chromosomally abnormal pregnancy at 11-13 weeks," Am. J. Obstet. Gynecol., 200:508.e1-508.e6 (2009).

Poon et al., "Maternal serum placental growth factor (P1GF) in small for gestational age pregnancy at $11^{+0}$ to $13^{+6}$ weeks of gestation," Prenat. Diagn., 28:1110-15 (2008).

Poon et al., "Prenatal detection of fetal Down's syndrome from maternal plasma," Lancet, 356:1819-20 (2000).

Roberts et al., "Pathogenesis and genetics of pre-eclampsia," Lancet, 357:53-56 (2001).

Savvidou et al., "First trimester urinary placental growth factor and development of pre-eclampsia," BJOG, 116:643-647 (2009).

Sibai et al., "Obstetrics: Risk factors for preeclampsia in healthy nulliparous women: A prospective multicenter study," Am. J. Obstet. Gynecol. 172:642-648 (1995).

Sibai et al., "Risk factors associated with preeclampsia in healthy nulliparous women," Am. J. Obstet. Gynecol., 177:1003-10 (1997).

Spencer et al., "First trimester maternal serum placenta growth factor (P1GF) concentrations in pregnancies with fetal trisomy 21 or trisomy 18," Prenat. Diagn., 21:718-722 (2001).

Spencer et al., "Free beta human choriogonadotropin in Down's syndrome screening: a multicentre study of its role compared with other biochemical markers," Ann. Clin. Biochem., 29:506-518 (1992).

Su et al., "Raised maternal serum placenta growth factor concentration during the second trimester is associated with Down syndrome," Prenat. Diagn., 22:8-12 (2002).

Supplementary European Search Report; Application No. 09704269.1-1223 / 2245180; mailed May 26, 2011; 1 page.

Than et al., "Application of pregnancy-related proteins in prenatal and tumor diagnostics—a workshop report," Placenta, 26(Suppl A):S110-S113 (2005).

Than et al., "Prediction of preeclampsia—a workshop report," Placenta, 29(Suppl A):S83-S85 (2008).

Yu et al., "Prediction of pre-eclampsia by uterine artery Doppler imaging: relationship to gestational age at delivery and small-for-gestational age," Ultrasound Obstet. Gynecol., 31:310-313 (2008).

Zaragoza et al., "Maternal serum placental growth factor at 11-13 weeks in chromosomally abnormal pregnancies," Ultrasound Obstet. Gynecol., 33:382-386 (2009).

Chinese Office Action; Application No. 200980110513.5; issued Jan. 14, 2013; Applicant: PerkinElmer Health Sciences, Inc.; Wallac Oy; The Fetal Medicine Foundation; Nicolaides Kypros; 2 pages.

Australian Office Action, Application No. 2009206243; issued Aug. 21, 2013; Applicants: Wallac Oy, The Fetal Medicine Foundation, Perkinelmer Health Sciences, Inc., Kypros Nicolaides; 5 pages.

METHODS FOR DETERMINING THE RISK OF PRENATAL COMPLICATIONS

CROSS REFERENCE TO RELATED APPLICATIONS

This application is a divisional of U.S. application Ser. No. 12/864,625, filed on Jul. 26, 2010, which is a National Stage application under 35 U.S.C. §371 and claims the benefit under 35 U.S.C. §119(a) of International Application No. PCT/US2009/032062, having an International Filing Date of Jan. 26, 2009, which claims the benefit of priority of U.S. Provisional Application No. 61/023,776, filed on Jan. 25, 2008; U.S. Provisional Application No. 61/025,890, filed on Feb. 4, 2008; U.S. Provisional Application No. 61/060,048, filed on Jun. 9, 2008; and U.S. Provisional Application No. 61/060,732, filed on Jun. 11, 2008, all of which are incorporated herein in their entirety.

BACKGROUND

At least 126 million women give birth every year worldwide. Over 20 million of them experience a pregnancy related complication or illness. For example, hypertensive disorders such as pre-eclampsia affect more than 10% of all pregnancies and are a leading cause of maternal death. Adequate prenatal health care decreases the chances that such complications and illnesses will go unnoticed. In many countries, screening methods for determining the risk of prenatal complications and/or fetal abnormalities have become routine to aid in treating and advising pregnant women. For example, throughout Europe, the United States and some regions in Asia, health care providers commonly screen for chromosomal abnormalities in the fetus using biochemical markers present in maternal blood. Such screening is helpful for identifying women who have sufficiently high risk to justify further diagnostic testing, which can be invasive and carry risk to the fetus. Maternal blood and other fluids also contain biochemical markers that can be used to detect pregnancy related illnesses of the woman. Even so, currently no routine screens have been adopted for early detection of pre-eclampsia using maternal samples. Thus, there exists the need to develop accurate screening methods for prenatal complications and/or fetal abnormalities.

SUMMARY

The present disclosure provides a method for determining the risk of pre-eclampsia in a pregnant individual. The method involves determining the amount of one or more biochemical markers selected from placental growth factor (PlGF) and pregnancy-associated plasma protein A (PAPP-A) in one or more blood samples from the individual; determining the blood pressure of the individual; and determining the risk of pre-eclampsia using the amount of each of the selected one or more biochemical markers and the blood pressure of the individual. In an embodiment, the method further involves determining uterine artery pulsatility index (PI) of the individual; and determining the risk of pre-eclampsia using the amount of each of the selected one or more biochemical markers and the blood pressure of the individual, and the PI. In an embodiment, the type of pre-eclampsia can be early pre-eclampsia. Late pre-eclampsia can also be detected using the methods. In an embodiment, the biochemical marker can be, for example, PlGF. In another embodiment, it can be PAPP-A. In a further embodiment, the method can employ both PlGF and PAPP-A. In an embodiment, the method can also include determining the amount of placental protein 13 (PP13) and determining the risk of pre-eclampsia using the amount of each of the selected one or more biochemical markers, the blood pressure of the individual and amount of PP13. The blood pressure can be, for example, mean arterial blood pressure.

In an embodiment the risk determination can include determining a likelihood ratio for blood pressure. Determining the risk can also include calculating a final risk based on the individual's prior risk of developing pre-eclampsia and a set of likelihood ratios based he amounts of the one or more biochemical markers and the blood pressure. In an embodiment, a multivariate Gaussian analysis is performed to determine the likelihood ratios. In an embodiment, the method can further involve using likelihood ratios for one or more maternal history parameters selected from race, smoking, parity, BMI, hypertension, previous pre-eclampsia, and mother/sister with previous pre-eclampsia. In an embodiment, the risk of pre-eclampsia in an individual has a detection rate of at least about 65% and a false positive rate of about 10%. In another embodiment, the risk of pre-eclampsia in an individual has a detection rate of at least about 75% and a false positive rate of about 10%. In a further embodiment, the risk of pre-eclampsia in an individual has a detection rate of at least about 90% and a false positive rate of about 10%. In yet another embodiment, the method for determining the risk of pre-eclampsia in an individual has a detection rate of at least about 95% and a false positive rate of about 10%.

Also provided by the present disclosure is a medical profile for a pregnant individual, which includes information such as the amounts of one or more biochemical markers present in one or more blood samples from the individual, the biochemical markers selected from placental growth factor (PlGF) and pregnancy-associated plasma protein A (PAPP-A); and the blood pressure of the individual, wherein the medical profile is stored on a computer-readable medium.

Additionally provided is an apparatus for determining the risk of pre-eclampsia in a pregnant individual. The apparatus includes a data input means for inputting the amounts of one or more biochemical markers selected from placental growth factor (PlGF) and pregnancy-associated plasma protein A (PAPP-A) in one or more blood samples from the individual, and the blood pressure of the individual; and a calculation means for determining the risk of developing pre-eclampsia using the input amounts of the biochemical markers and the blood pressure. In an embodiment, the apparatus also can include a data input means for inputting one or more parameters selected from age, race, smoking, parity, BMI, hypertension, previous pre-eclampsia, and mother/sister with previous pre-eclampsia, and PI, and a calculation means for determining the risk of developing pre-eclampsia using the input amounts of the biochemical markers, the blood pressure and one or more selected parameter.

The present disclosure provides a method for determining the risk of a chromosomal abnormality in a fetus. The method involves determining the amount of placental growth factor (PlGF), pregnancy-associated plasma protein A (PAPP-A) and free human chorionic gonadotropin (free beta hCG) in one or more blood samples taken from a pregnant individual; and determining the risk of the chromosomal abnormality in the fetus using the measured amounts of PlGF, PAPP-A, and free beta hCG. In an embodiment, the chromosomal abnormality is selected from the group consisting of trisomy 21, trisomy 18, trisomy 13, Turner syndrome, and triploidy. In an embodiment, the method can include determining one or more ultrasound markers of the fetus and determining the risk of the chromosomal abnormality in the fetus using the amounts of PlGF, PAPP-A, free beta hCG, and the one or more ultrasound marker. The ultrasound marker can be, for example, nuchal translucency. In an embodiment, the method also can involve determining the amount of at least one biochemical marker selected from placental protein 13 (PP13) and metalloprotease 12 (ADAM12), and determining the risk of the chromosomal abnormality in the fetus using the amounts of PlGF, PAPP-A, free beta hCG, and the at least one biochemical marker. In an embodiment, the one or more biological samples are taken from the pregnant individual in the first trimester of pregnancy, for example, within weeks 10 to 19 of pregnancy, such as weeks 11 to 13 of pregnancy. In an embodiment, the determining includes calculating a final risk based on the prior risk of developing a chromosomal abnormality and a set of likelihood ratios based on the amounts of PlGF, PAPP-A, and free beta hCG. Optionally, a multivariate Gaussian analysis is performed to determine the likelihood ratios. In an embodiment, likelihood ratios are also used for one or more maternal history parameters.

Provided in the present disclosure is a medical profile for a pregnant individual, which includes information for determining risk of a chromosomal abnormality in a fetus, wherein the information includes the amounts of PlGF, PAPP-A, and free beta hCG in one or more blood samples from the pregnant individual, and wherein the medical profile is stored on a computer-readable medium. The medical profile further can include additional information for determining the risk of developing pre-eclampsia, wherein the additional information includes the blood pressure of the pregnant individual.

Provided also is an apparatus for determining risk of a chromosomal abnormality in a fetus. The apparatus includes a data input means for inputting the amounts of PlGF, PAPP-A, and free beta hCG in one or more blood samples obtained from a pregnant individual; and a calculation means for determining the risk of a chromosomal abnormality in a fetus using the amounts of the PlGF, PAPP-A, and free beta hCG. In an embodiment, the apparatus further includes means for inputting at least one of the amounts of ADAM12 and PP13 in one or more blood samples obtained from the pregnant individual; and determining the risk of a chromosomal abnormality in a fetus using the amounts of at least one of the amounts of ADAM12 and PP13, and the amounts of PlGF, PAPP-A, and free beta hCG. In an embodiment, the apparatus further determines risk of developing pre-eclampsia, and includes a data input means for inputting a blood pressure of the pregnant individual; and a calculation means for determining the risk of pre-eclampsia using the input amounts of one or more of PlGF and PAPP-A, and the blood pressure.

Commercial packages, or kits, are also provided for carrying out the methods described herein for determining risk of pre-eclampsia and chromosomal abnormalities. The kits contain reagents for specifically detecting the amounts of selected combinations of biochemical markers.

DETAILED DESCRIPTION

Figure 1:
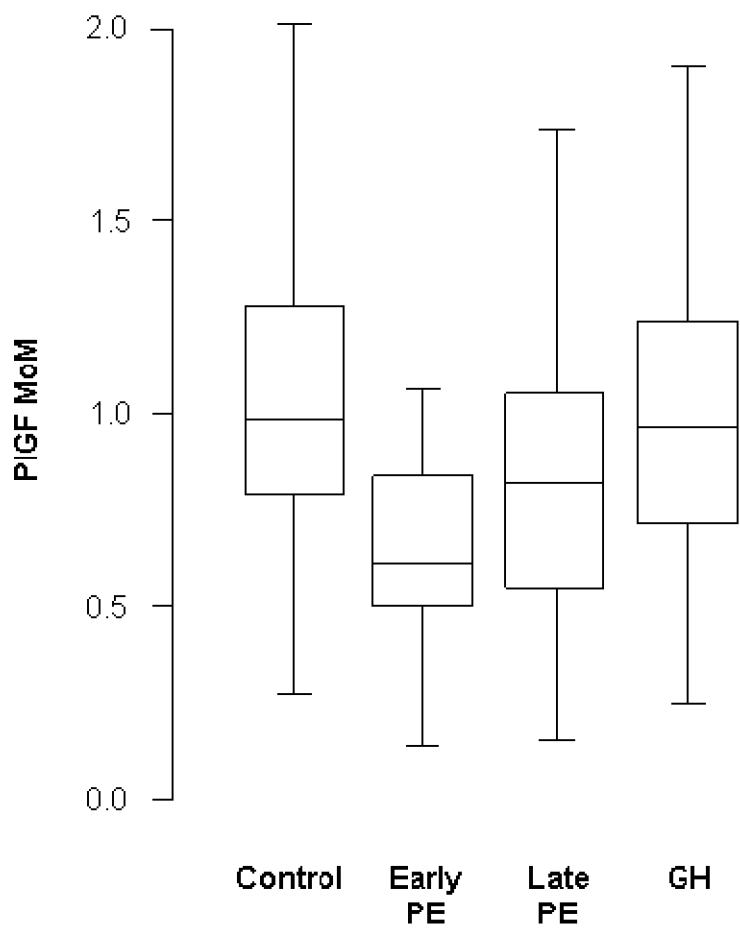
FIG. 1 is a box-whisker plot of placental growth factor (PlGF) multiple of the median (MoM) in four pregnancy outcome groups: control, early pre-eclampsia (PE), late PE, gestational hypertension (GH), which shows that the amount of PlGF in biological samples from pregnant individuals is lower when the individual has early pre-eclampsia and late pre-eclampsia, and somewhat lower when the individual has gestational hypertension.

Methods, apparatus, medical profiles and kits described herein are useful for determining the risk that a pregnant individual will develop pre-eclampsia (PE) and related placental disorders. As is described, this risk can be determined based on the amounts of biochemical markers such as placental growth factor (PlGF) and pregnancy-associated plasma protein A (PAPP-A) present in a biological sample taken from the pregnant individual, in combination with the blood pressure of the pregnant individual. Additional biochemical markers, such as PP13, and biophysical markers, such as uterine artery pulsatility index, as well as maternal history parameters, can also be used when determining the risk of pre-eclampsia according to methods described herein.

Also described herein are methods, apparatus, medical profiles, and kits useful for determining the risk that a pregnant individual is carrying a fetus having a chromosomal abnormality (CA), such as Down Syndrome. As is described, the risk can be determined based on the amounts of PlGF, PAPP-A, and free human chorionic gonadotropin (free beta hCG) present in biological sample taken from the pregnant individual. Additional biochemical markers and biophysical markers (such as fetal ultrasound markers), as well as maternal history parameters, can also be used when determining the risk of chromosomal abnormalities according to methods described herein.

As is described in Example 1, statistical analysis of a clinical population was performed, revealing that combinations of biochemical markers, including PAPP-A, PlGF and PP13, and biophysical markers, including blood pressure and uterine Doppler pulsatility index, were remarkably effective for determining risk of pre-eclampsia with clinically acceptable detection and false positive rates. For example, PlGF and blood pressure, with or without taking into consideration maternal factors, provided 68% detection with 10% false positives. Additional specific non-limiting examples for determining risk of early and late pre-eclampsia include: PAPP-A and blood pressure; PlGF and PAPP-A and blood pressure; PlGF, PAPP-A, PP13 and blood pressure; PlGF and PP13 and blood pressure; PAPP-A and PP13 and blood pressure, (for detection rates, see, for examples, Tables 4, 6 and 10 for early pre-eclampsia and Tables 7 and 10 for late pre-eclampsia). As used herein the "% detection" is the percentage-expressed proportion of affected (for example, pre-eclamptic) individuals with a positive result. The "% false positive" is the percentage-expressed proportion of unaffected individuals with a positive result. The predictive power of a marker or combination thereof is commonly expressed in terms of the detection rate for a given false positive rate.

The selection of a particular combination of biochemical and biophysical markers, from those described herein, to be used in a clinical or other laboratory settings can depend on a variety of practical considerations, including the available medical equipment and biochemical marker testing reagents in the particular setting. For example, at settings where Doppler ultrasound is available, a health care provider would likely include PI when determining risk of pre-eclampsia. In medical environments not equipped with advanced equipment (such as Doppler ultrasound), a clinical acceptable risk assessment can be made using blood pressure and levels of biochemical markers, as is described herein.

Also as described herein is the finding that the amount of the biochemical marker PlGF in maternal blood has predictive power for determination of risk of chromosomal abnormalities of the fetus. As such, when a screening test for chromosomal abnormalities includes testing of PlGF, it is possible to also determine risk of pre-eclampsia. To accomplish this, all that would be needed is a maternal blood pressure reading. Additional parameters that would normally be collected in the course of prenatal screening and be used routinely when determining risk of fetal chromosomal abnormalities also can be used when determining risk of pre-eclampsia. As is described in Example 3, when employing the methods for determining risk of pre-eclampsia, risk of related disorders, such as fetal growth restriction, preterm birth and gestational hypertension can also be determined.

As used herein, the term "pre-eclampsia" means the disorder of pregnancy characterized in part by gestational hypertension and proteinuria. For previously normotensive women, PE is typically defined as gestational hypertension with proteinuria and severe PE as sever gestational hypertension with proteinuria. For women with chronic hypertension, superimposed PE is typically defined as the new development of proteinuria. Aspects of PE useful for making a diagnosis of PE can be classified according to guidelines set out by various medical organizations. For example, gestational hypertension, according to guidelines of the International Society for the Study of Hypertension in Pregnancy (Davey et al., Am. J. Obstet Gynecol; 158; 892098, 1988), is described as two recordings of diastolic blood pressure of 90 mmHg or higher at least 4 h apart, and sever hypertension as pressure of at least 110 mm Hg or higher at least 4 h apart or one recording of diastolic blood pressure of at least 120 mm Hg. Proteinurea is defined as excretion of 300 mg or more in 24 h or two readings of 2+ or higher on dipstick analysis of midstream or catheter urine specimens if no 24 h collection was available. Women are classified as previously normotensive or with chromic hypertension generally before 20 weeks gestation. Pre-eclampsia is understood to be a disorder on a spectrum of related disorders, including intrauterine growth retardation, early miscarriage, preterm birth and intrauterine death. Although not wishing to be bound by theory, it has been proposed that intrauterine growth retardation reflects an adaptation of the pregnant woman's body to cope with the condition of pre-eclampsia, which allows the fetus to survive. Early miscarriage and preterm birth, on the other hand, may reflect adaptation of the pregnant woman's body to cope with the condition of pre-eclampsia, which allow the woman to survive. In this context, intrauterine death would be a failure of this adaptation. Thus, the methods described herein for determining risk of pre-eclampsia can also be used to determine risk of pre-eclampsia-related disorders on the pre-eclampsia spectrum.

In instances where a pregnant individual is determined to have an increased risk of developing pre-eclampsia using a method as described herein, the individual can receive therapy or lifestyle advice from a health care provider. Although there is no widely used treatment for pre-eclampsia, various studies have shown the benefit of therapies such as anti-hypertensive drugs, such as magnesium sulphate, aspirin, diazepam, and phenytoin; and dietary supplements, such as vitamin D, calcium, and selenium.

Pre-eclampsia can develop as early as 20 weeks of gestation and is generally considered "early pre-eclampsia" when it develops before about 32-34 weeks of gestation, and "late pre-eclampsia" when it develops after about 32-34 weeks of gestation. Early pre-eclampsia is associated with increased morbidity and thus is considered a more severe form of pre-eclampsia. The methods for determining the risk of PE described herein are useful for screening for "early pre-eclampsia" and "late pre-eclampsia." As is described herein, for instance in Example 1, the methods for determining risk of pre-eclampsia are effective during less than 34 weeks of gestation, inclusive; less than 36 weeks of gestation, inclusive, such as 34 to 36 weeks of gestation, inclusive, less than 37 weeks gestation, inclusive, and greater an 37 weeks of gestation, inclusive.

Examples 1 to 3 describe that risk of early and late pre-eclampsia (<34 weeks, 32-34 weeks and 37+ weeks) can be determined using particular biochemical and biophysical markers, using blood samples that were collected between 11 and 19 weeks of gestation. Thus, for use in the methods for detecting pre-eclampsia, a sample can be collected between about 11 and 37 weeks gestation, inclusive, including between about 11 and 20 weeks, inclusive, between about 11 and 34 weeks, between about 20 and 34 weeks, and more generally, prior to about 20 weeks, within first trimester after about 10 weeks, within second trimester and within third trimester. Although earlier testing is often a beneficial policy from a public health perspective, it is understood that collection of samples can sometimes be affected by practical considerations such as a woman delaying a visit to her health care provider until relatively later weeks of gestation.

In certain circumstances, biological samples can be collected on more than one occasion from a pregnant individual, for example, when her hypertensive and/or placental condition requires monitoring for development of pre-eclampsia due to a priori risk, presentation of symptoms and/or other factors. The methods for determining risk of pre-eclampsia described herein can also be used for monitoring a pregnant individual who is undergoing a therapy or treatment for a hypertensive and/or placental condition. If desired, testing of biochemical and/or biophysical markers can be carried out in a home setting, such as by using dipstick biochemical test formats and automated blood pressure machines for home use.

The methods for determining the risk of pre-eclampsia in a pregnant individual involve determining the amount of one or more biochemical markers selected from PlGF and PAPP-A. The amounts of additional biochemical markers, such as PP13, also can be used in the methods. As used herein, the term "PlGF" means the mammalian growth factor having an amino acid sequence homologous to GenBank accession number P49763. As used herein, the term "PAPP-A" means the metzincin metalloproteinase known as Pregnancy-associated plasma protein A and having an amino acid sequence homologous to GenBank accession number AAH78657. As used herein, the term "PP13" means placental protein 13, also known as galectin-13 having an amino acid sequence homologous to GenBank accession number NP_037400.

The methods described herein involve determining blood pressure of an individual. One or more of systolic blood pressure, diastolic blood pressure and mean arterial blood pressure of the pregnant individual can be used. Mean arterial pressure (MAP) refers to the average blood pressure over a cardiac cycle and is determined by the cardiac output (CO), systemic vascular resistance (SVR), and central venous pressure (CVP), using established procedures. A health care provider can use any method to measure the blood pressure of the pregnant individual, including, for example, palpation methods, auscultatory methods and oscillometric methods. Automated blood pressure measuring equipment also can be used. The methods described herein also can involve determining uterine artery pulsatility index (PI), which is an arterial blood-flow velocity waveform index for quantifying pulsatility or oscillations of the waveform. The PI of the pregnant individual can be measured using any known method. For example, uterine artery Doppler ultrasonography can be performed via the transvaginal or transabdominal route. The uterine artery is first identified with the use of color Doppler ultrasonography. Pulsed-wave Doppler ultrasonography can then be used to obtain waveforms. Various indices can then be calculated. For example PI can be calculated as the peak systolic flow minus the end diastolic flow divided by the mean flow.

The methods for determining the risk of pre-eclampsia in a pregnant individual involve using a biological sample from the pregnant individual. The biological sample can be any body fluid or tissue sample that contains the selected biochemical markers. Examples 1 to 3 describe use of maternal blood in the form of serum. The choice of biological sample can often depend on the assay formats available in a particular clinical laboratory for testing amounts of markers. For example, some assay formats lack sensitivity needed for assaying whole blood, such that a clinical laboratory opts for testing a fraction of blood, such as serum, or using dried blood. Exemplary biological samples useful for the methods described herein include blood, purified blood products (such as serum, plasma, etc.), urine, amniotic fluid, a chorionic villus biopsy, a placental biopsy and cervicovaginal fluid. Amounts of biochemical markers present in a biological sample can be determined using any assay format suitable for measuring proteins in biological samples. A common assay format for this purpose is the immunoassay, including, for example, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); dissociation-enhanced lanthanide fluorescent immunoassay (DELFIA) and chemiluminescence assays (CL).

To determine whether the amount of biochemical markers is greater than or less than normal, the normal amount of biochemical marker present in a maternal biological sample from a relevant population is determined. The relevant population can be defined based on any characteristics than can affect normal (unaffected) amounts of the markers. For determining risk of pre-eclampsia, the relevant population can be established on the basis of low risk for pre-eclampsia. Once the normal marker amounts are known, the determined marker amounts can be compared and the significance of the difference determined using standard statistical methods. When there is a statistically significant difference between the determined marker amount and the normal amount, there is a significant risk that the tested individual will develop pre-eclampsia.

The risk that a pregnant individual develops pre-eclampsia or is carrying a fetus having a chromosomal abnormality can be determined from biochemical marker amounts using statistical analysis based on clinical data collected in a patient population study. Examples 1 to 3 show results from such studies. There are multiple statistical methods for combining parameters that characterize the pregnant individual, such as amounts of biochemical markers, to obtain a risk estimate. The likelihood method (Palomaki and Haddow, 1987) and the linear discriminant function method (Norgarrd-Pedersen et al. Clin. Genet. 37, 35-43 (1990)) are commonly used for this purpose. The basic principle of the likelihood method is that the population distributions for a parameter (such as the amount of a biochemical marker) are known for the 'unaffected' and 'affected' groups. Thus, for any given parameter (such as amount of marker and blood pressure reading), the likelihood of membership of the 'unaffected' and 'affected' groups can be calculated. The likelihood is calculated as the Gaussian height for the parameter based on the population mean and standard deviation. The 'likelihood ratio' is the ratio of the heights calculated using 'unaffected' and 'affected' population parameters, and is an expression of the increased risk of having a disorder, with respect to a prior risk.

A woman's prior odds (which is a statistical expression related to prior risk, as is described herein below) for having pre-eclampsia or carrying a fetus with a chromosomal abnormality can be calculated using a formula derived by clinical population studies (Cuckle et al. 1987). These prior odds can be modified using the likelihood ratio to derive the posterior odds that can be used for the pre-eclampsia or chromosomal abnormality risk estimate. A detailed description of use of the likelihood method for predicting risk that a fetus has a chromosomal abnormality is set forth, for example, in "Screening for Down's Syndrome," ed. J. G. Grudzinskas, T. Chard, M. Chapman and H. Cuckle; Published by Cambridge University Press, 1994). It is also possible to use observed distributions of likelihood ratios for determining risk using the methods described herein (see, for example, Spencer et al., Ann. Clin. Biochem. 29, 506-18 (1992)).

An overview for determining risk in accordance with the methods described herein follows: An exemplary starting point is determining the prior odds. In the case of chromosomal abnormality risk, the prior odds are typically derived from the maternal age using an age-risk formula. In the case of risk of pre-eclampsia the prior odds are typically derived from a general population risk. In current chromosomal abnormality screening practice, biochemical marker values are being referred to smoothed median values to produce adjusted multiple of the median (MoM) values to standardise for factors such as assay, gestation, maternal weight, smoking status, and the like. This is done, for example, because the amounts of biochemical markers in the individual's body change with gestation, in order to calculate risks, the biochemical marker value is adjusted to be unaffected by gestational age. The value of a MoM for a sample is the ratio of the biochemical marker value to the population median value at the same gestational age (or other parameter). The Gaussian heights for biochemical marker results are determined for the 'unaffected' and 'affected' population parameters. The ratio of the height on the 'unaffected' curve and the height on the 'affected' curve is determined. The prior odds are multiplied by this ratio.

Conceptually, calculating risk using three biochemical markers requires first that individual likelihood ratios be defined for each of the markers (first corrected for maternal age) and then multiplied together. An additional factor is needed in the calculation, however, to account for the extent of overlap of information (correlation) of the three individual biochemical markers. Typically r-values are used to express the correlation between parameters, such as our example of three individual biochemical markers. Example 1 provides r values corresponding to correlations between various parameters relevant to calculating risk of pre-eclampsia. Example 4 provides r values corresponding to correlations between various parameters relevant to calculating risk of fetal chromosomal abnormalities. Other variables have been found to influence maternal blood levels of particular markers, and these variables can be adjusted for, and the adjustments incorporated into the final expression of the values as MoMs.

As is described in Example 1, statistical analyses of clinical data, including amounts of biochemical markers such as PlGF, PAPP-A, PP13, and biophysical markers such as blood pressure and PI, were carried out to determine the risk of a pregnant individual developing pre-eclampsia. Notably, the presently described methods express blood pressure as a likelihood ratio. This is a unique approach for determining a risk of pre-eclampsia. Although in prior clinical practice, it is common for a health care provider to take a blood pressure reading when attending to a pregnant patient during an office visit, the use of blood pressure in an algorithm for determining risk of pre-eclampsia has been until now overlooked.

In an embodiment, the statistical process for carrying out the risk estimate can be summarized as shown below. For each biochemical and biophysical marker, a MoM is calculated. The MoM(s) are then adjusted based on maternal history parameters such as race, smoking, parity, BMI, hypertension, previous pre-eclampsia, and mother/sister with previous pre-eclampsia. Multivariate Gaussian analysis is then performed to determine likelihood ratios. For pre-eclampsia risk determination, the prior risk was based on general population risk.

1. prior risk=1 in x
2. Likelihood Ratio (LR)-race=2.18 if black, 0.57 otherwise
3. LR-smoke=0.56 if smoker, 1.04 otherwise
4. LR-para=1.34 if para 0, 0.66, 0.63 & 1.14 for 1, 2 and 3+
5. LR-BMI=0.65 if <25, 1.23 & 3.05 for 25-34 and 35+
6. LR-hypertension=10.24 if disease, 0.94 otherwise
7. LR-history=7.87 if previous PE pregnancy, 0.64 if none, 1 if para 0
8. LR-family=2.89 if mother had PE pregnancy, 0.92 otherwise
9. LR-biochemical marker (PlGF, PAPP-A, PP13, etc.) and physical marker profile (blood pressure or PI)=ratio of heights of multivariate Gaussian frequency distributions in early-PE and unaffected pregnancies. The parameters of the distributions are for each marker, means and SDs, and for pairs of markers, the r-values.
10. The final risk calculated by expressing the prior risk as an odds (1:x−1), multiplying the left hand side by all the LRs and reforming as 1 in y. To calculate posterior risks the prior risk is first expressed as an odds. Thus 1 in x becomes 1:(x−1). The prior odds are multiplied by the LR to give LR:(x−1), which is still add odds. We can rewrite it as the odds 1:(x−1)/LR and convert it into a risk of 1 in [(1:(x−1)/LR]+1.

In other embodiments, the risk of pre-eclampsia can be determined with fewer or without inclusion of prior risk factors (see for example, Tables 4 and 6).

It is understood that the number values can be different for different study populations, although those shown below provide an acceptable starting point for risk calculations. For example, it has been observed that for a particular clinical center carrying out patient risk analysis, the number values in a risk algorithm can drift over time, as the population in the served region varies over time.

Thus, the present disclosure provides a method for determining the risk of pre-eclampsia in a pregnant individual. The method involves determining the amount of one or more biochemical markers selected from placental growth factor (PlGF) and pregnancy-associated plasma protein A (PAPP-A) in one or more biological samples from the individual; determining the blood pressure of the individual; and determining the risk of pre-eclampsia using the amount of each of the selected one or more biochemical markers and the blood pressure of the individual. In an embodiment, the method further involves determining uterine artery pulsatility index (PI) of the individual; and determining the risk of pre-eclampsia using the amount of each of the selected one or more biochemical markers and the blood pressure of the individual, and the PI. In an embodiment, the type of pre-eclampsia can be early pre-eclampsia. Late pre-eclampsia can also be detected using the methods. The biochemical marker can be, for example, PlGF. In another embodiment, it can be PAPP-A. In a further embodiment, the method can employ PlGF and PAPP-A. In an embodiment, the method can also include determining the amount of placental protein 13 (PP13) and determining the risk of pre-eclampsia using the amount of each of the selected one or more biochemical markers, the blood pressure of the individual and amount of PP13. The blood pressure can be, for example, mean arterial blood pressure.

In an embodiment the risk determination can include determining a likelihood ratio for blood pressure. Determining the risk can also include calculating a final risk based on the individual's prior risk of developing pre-eclampsia and a set of likelihood ratios based he amounts of the one or more biochemical markers and the blood pressure. In an embodiment, a multivariate Gaussian analysis is performed to determine the likelihood ratios. In an embodiment, the method can further involve using likelihood ratios for one or more maternal history parameters selected from race, smoking, parity, BMI, hypertension, previous pre-eclampsia, and mother/sister with previous pre-eclampsia. In an embodiment, the risk of pre-eclampsia in an individual has a detection rate of at least about 65% and a false positive rate of about 10%. In another embodiment, the risk of pre-eclampsia in an individual has a detection rate of at least about 75% and a false positive rate of about 10%. In a further embodiment, the risk of pre-eclampsia in an individual has a detection rate of at least about 90% and a false positive rate of about 10%. In yet another embodiment, the method for determining the risk of pre-eclampsia in an individual has a detection rate of at least about 95% and a false positive rate of about 10%.

Also provided by the present disclosure is a medical profile for a pregnant individual, which includes information such as the amounts of one or more biochemical markers present in one or more biological samples from the individual, the biochemical markers selected from placental growth factor (PlGF) and pregnancy-associated plasma protein A (PAPP-A); and the blood pressure of the individual, wherein the medical profile is stored on a computer-readable medium.

Additionally provided is an apparatus for determining the risk of pre-eclampsia in a pregnant individual. The apparatus includes a data input means for inputting the amounts of one or more biochemical markers selected from placental growth factor (PlGF) and pregnancy-associated plasma protein A (PAPP-A) in one or more biological samples from the individual, and the blood pressure of the individual; and a calculation means for determining the risk of developing pre-eclampsia using the input amounts of the biochemical markers and the blood pressure. In an embodiment, the apparatus also can include a data input means for inputting one or more parameters selected from age, race, smoking, parity, BMI, hypertension, previous pre-eclampsia, and mother/sister with previous pre-eclampsia, and PI, and a calculation means for determining the risk of developing pre-eclampsia using the input amounts of the biochemical markers, the blood pressure and one or more selected parameter.

In another aspect of the methods described herein, provided is a method for determining the risk of a chromosomal abnormality in a fetus. Determining the risk of a fetal chromosomal abnormality as described herein involves determining the amounts of PlGF, PAPP-A, and free beta hCG in one or more biological samples taken from the pregnant individual and determining the risk of the chromosomal abnormality in a fetus based on the amounts of PlGF, PAPP-A, and free beta hCG The method can further include measuring the amount of ADAM12 in a biological sample taken from the pregnant individual, and using the measured amount of ADAM12, together with the parameters described above, to determine the risk of fetal chromosomal abnormality.

As is described in Example 4, statistical analysis of a clinical population was performed, revealing that combinations of biochemical markers, including PAPP-A, PlGF and free beta hCG, and biophysical markers, including fetal nuchal translucency (NT), were remarkably effective for determining risk of chromosomal abnormality of a fetus with clinically acceptable detection and false positive rates. For example, Free beta hCG, PAPP-A, and PlGF had a detection rate of about 70% with a 5% false positive rate. By including maternal age in a risk determination using the same biochemical marker set, a detection rate of 80% with 5% false positive rate was achieved.

As is used herein, the term "chromosomal abnormality" means an atypical number of chromosomes or a structural abnormality in one or more chromosomes. The term encompasses annupluidy such as trisomy 21 (Down Syndrome), trisomy 18 (Edwards Syndrome), and trisomy 13 (Patau Syndrome) as well as chromosomal deletion such as Turner syndrome, that can be detected by the presence of abnormal amounts of PlGF, PAPP-A and free beta hCG in a maternal sample. As used herein, the term "free beta hCG" means the beta subunit of is a glycoprotein hormone produced during pregnancy by the embryo just after conception and later by the syncytiotrophoblast, and having an amino acid sequence homologous to GenBank accession number NM_000737. Example 4 shows that the combination of PlGF, PAPP-A and free beta hCG is useful for detecting trisomy 21, trisomy 18, trisomy 13, Turner Syndrome and triploidy (see FIG. 7).

The methods described herein for determining the risk of a chromosomal abnormality in a fetus can also include determining a biophysical marker of the fetus. The biophysical marker can be, for example, an ultrasound marker, such as nuchal translucency (NT) of the fetus. Nuchal translucency is a well known biophysical marker of the fetus and is defined as the space from the back of the fetal neck to the skin overlying the neck and it refers to an observation that abnormal foetuses tend to show an accumulation of fluid in this region and have an increased risk of having a variety of chromosome abnormalities present, including the common finding of Down's Syndrome. An ultrasound NT scan is normally performed in the first trimester.

The methods described herein for determining the risk of a chromosomal abnormality in the fetus can be performed in the first trimester of pregnancy, and/or in the second trimester of pregnancy. Thus, the biological sample can be taken from the pregnant individual at a time between about weeks 10 and 20, between about weeks 10 and 18, between about weeks 10 and 16 (inclusive) of gestation, such as between weeks 11 and 13 (inclusive) of gestation.

As is described in Example 4, statistical analyses of clinical data, including amounts of biochemical markers such as PlGF, PAPP-A, and free beta hCG and biophysical markers such as fetal NT, were carried out to determine the risk of chromosomal abnormality of a fetus. An exemplary statistical process for carrying out the risk estimate based on PlGF, PAPP-A and free beta hCG can be summarized as shown below.

PlGF is expressed in MoMs and weight corrected.
1. A prior risk (expressed as odds) is derived from the maternal age-specific prevalence (and family history of Down syndrome, if applicable).
2. This is multiplied by an LR from the log Gaussian distributions of PlGF in Down syndrome and unaffected pregnancies.
3. The unaffected distribution parameters are SD=0.185.
4. Down syndrome mean and SD are mean=$\log_{10}(0.566)$=−0.247 and SD=0.186.
5. The final odds are converted back into a risk.
6. For combinations of PlGF with PAPP-A and free beta hCG, correlation coefficients between the log MoM values in Down syndrome and unaffected pregnancies are needed. Unaffected pregnancies: with PAPP-A is 0.278; with free beta hCG it is 0.085. Down syndrome values are: 0.334 and 0.098.
7. Zero correlation with NT can be assumed.
8. Mean=$\log_{10}$ (0.538)=−0.269; SD=0.226; correlation with PAPP-A=0.056 and with free beta hCG=−0.142
  The algorithm and methodology described above can be altered for any annuploidy.

It is understood that the number values can be different for different study populations, although those shown below provide an acceptable starting point for risk calculations. For example, it has been observed that for a particular clinical center carrying out patient risk analysis, the number values in a risk algorithm can drift over time, as the population in the served region varies over time.

Thus, the present disclosure provides a method for determining the risk of a chromosomal abnormality in a fetus. The method involves determining the amount of placental growth factor (PlGF), pregnancy-associated plasma protein A (PAPP-A) and free human chorionic gonadotropin (free beta hCG) in one or more biological samples taken from a pregnant individual; and determining the risk of the chromosomal abnormality in the fetus using the measured amounts of PlGF, PAPP-A, and free beta hCG. In an embodiment, the chromosomal abnormality is selected from the group consisting of trisomy 21, trisomy 18, trisomy 13, Turner syndrome, and triploidy. In an embodiment, the method can include determining one or more ultrasound markers of the fetus and determining the risk of the chromosomal abnormality in the fetus using the amounts of PlGF, PAPP-A, free beta hCG, and the one or more ultrasound marker of the fetus. The ultrasound marker can be, for example, nuchal translucency. In an embodiment, the method also can involve determining the amount of at least one biochemical marker selected from placental protein 13 (PP13) and metalloprotease 12 (ADAM12), and determining the risk of the chromosomal abnormality in the fetus using the amounts of PlGF, PAPP-A, free beta hCG, and the at least one biochemical marker. In an embodiment, the one or more biological samples are taken from the pregnant individual in the first trimester of pregnancy, for example, within weeks 10 to 19 of pregnancy, such as weeks 11 to 13 of pregnancy. In an embodiment, the determining includes calculating a final risk based on the prior risk of developing the chromosomal abnormality and a set of likelihood ratios based on the amounts of PlGF, PAPP-A, and free beta hCG. Optionally, a multivariate Gaussian analysis is performed to determine the likelihood ratios. In an embodiment, likelihood ratios are also used for one or more maternal history parameters.

Provided in the present disclosure is a medical profile for a pregnant individual, which includes information for determining risk of a chromosomal abnormality in a fetus, wherein the information includes the amounts of PlGF, PAPP-A, and free beta hCG in one or more biological samples from the pregnant individual, and wherein the medical profile is stored on a computer-readable medium. The medical profile further can include additional information for determining the risk of developing pre-eclampsia, wherein the additional information includes the blood pressure of the pregnant individual.

Provided also is an apparatus for determining risk of a chromosomal abnormality in a fetus. The apparatus includes a data input means for inputting the amounts of PlGF, PAPP-A, and free beta hCG in one or more biological samples obtained from a pregnant individual; and a calculation means for determining the risk of a chromosomal abnormality in a fetus using the amounts of the PlGF, PAPP-A, and free beta hCG. In an embodiment, the apparatus further includes means for inputting at least one of the amounts of ADAM12 and PP13 in one or more biological samples obtained from the pregnant individual; and determining the risk of a chromosomal abnormality in a fetus using the amounts of at least one of the amounts of ADAM12 and PP13, and the amounts of PlGF, PAPP-A, and free beta hCG. In an embodiment, the apparatus further determines risk of developing pre-eclampsia, and includes a data input means for inputting a blood pressure of the pregnant individual; and a calculation means for determining the risk of pre-eclampsia using the input amounts of one or more of PlGF and PAPP-A, and the blood pressure. Additional data means for inputting biophysical markers, such as ultrasound markers including NT values, and maternal history information can be included, along with corresponding calculation means for determining risk of a chromosomal abnormality of the fetus and/or pre-eclampsia.

The present disclosure also provides commercial packages, or kits, for determining the risk that a pregnant individual will develop pre-eclampsia. Such kits can include one or more reagents for detecting the amount of at least one biochemical marker in a biological sample from a pregnant individual, wherein the at least one biochemical markers are selected from PlGF and PAPP-A; and optionally, instructions for carrying out the test. The kit can also include reagents for detecting other biochemical markers, such as PP13, MP3, TNFR1, ADAM12, and other biochemical markers. Exemplary specific kits contain reagents for detecting PlGF and PAPP-A; PlGF and PP13; PAPP-A and PP13; PlGF, PAPP-A and PP13; and combinations with other biochemical markers relevant to pre-eclampsia and related disorders.

A kit for determining the risk that a pregnant individual is carrying a fetus with a chromosomal abnormality can include reagents for measuring the amount of PlGF, PAPP-A, and free beta hCG in a biological sample taken from the pregnant individual; and optionally, instructions for carrying out the test.

A reagent for detecting the amount of a biochemical marker can be, for example, a binding partner that selectively recognizes the particular biochemical marker, such as an antibody, antibody portion, antibody-like material, protein-nucleic acid and the like.

Example 1

Clinical Study of the Role of PlGF, PAPP-A and Biophysical Markers for Detecting Pre-Eclampsia This example shows the usefulness of various combinations of biochemical and biophysical markers, including maternal blood pressure, uterine Doppler pulsatility index, PlGF, PAPP-A and PP13, for determining risk of pre-eclampsia in a pregnant individual.

A study was undertaken to screen for adverse pregnancy outcomes in women attending for routine assessment of risk for chromosomal abnormalities. Maternal characteristics and medical history were recorded and blood collected. Serum was stored at −80° C. for subsequent biochemical analysis. Written informed consent was obtained from the women agreeing to participate in the study, which was approved by King's College Hospital Ethics Committee. Additional information concerning clinical population and sample collection is provided in Example 3.

For the analyses described herein, all biochemical and biophysical markers were expressed in MoMs and $\log_{10}$ transformed. Expression of blood pressure (MAP) as a MOM is an approach unique to the present study.

Biochemical marker amounts and biophysical readings were MoMed as follows, where CRL is crown-rump length, BMI is body mass index, GA is gestation in days and maternal weight is in Kg:

PlGF/(277.908−6.97605GA+0.0477151GA×GA)
PP13/70.15/(0.30974+45.3179/weight)
MAP (blood pressure)/$10^{1.94359-0.00024649CRL}/10^{-0.111838+0.00590207BMI-0.0000574110BMI\times BMI}$
Doppler (PI)/$^{0.36683-0.00246CRL}/10^{0.02691-0.00105BMI}$ Means values for PlGF, PP13, PAPPA, MAP and Doppler PI, the values were −0.200, −0.078, −0.268, 0.051 & 0.197 respectively in early PE; and −0.002, 0.002, 0.009, 0.000 & 0.000 in unaffected pregnancies.

In the same order the standard deviations (SDs) were: 0.308, 0.200, 0.324, 0.047 & 0.137; and 0.185, 0.184, 0.236, 0.035 & 0.120.

R-values were as follows: Early PE: PlGF-PP13 0.194, PlGF-PAPPA 0.365, PlGF-MAP −0.142, PlGF-Doppler 0.199, PP13-PAPPA 0.389, PP13-MAP 0.065, PP13-Doppler −0.332, PAPPA-MAP 0.364, PAPPA-Doppler −0.295, MAP-Doppler −0.485.

Unaffected: PlGF-PP13 0.046, PlGF-PAPPA 0.278, PlGF-MAP −0.043, PlGF-Doppler −0.066, PP13-PAPPA 0.271, PP13-MAP −0.014, PP13-Doppler −0.089, PAPPA-MAP 0.000, PAPPA-Doppler −0.168, MAP-Doppler −0.075.

Biochemical markers considered were PAPP-A, PlGF and PP13 (using the PerkinElmer DELFIA immunoassay). The unaffected parameters for PAPP-A were from the entire data set including pregnancies not in the case-control series. All the parameters for PlGF and PP13 were from the case-control series.

Biophysical markers considered include parameters for MAP and uterine Doppler PI from the entire data set, although not all women had both measures. Correlation coefficients with the biochemical markers were used.

To express prior risk factors for pre-eclampsia, 1 ratios (LRs) were derived from the entire data set. The observed values are shown in Table 1 and compared with those observed in a previous study from the same center. The distribution of risk factors was unrelated to the severity of pre-eclampsia (Table 2) so the same LRs can be used for all subgroups.

For model predictions for biochemical and physical markers, multivariate log Gaussian fit were assumed. Table 3 shows the predicted detection rate (DR) for early pre-eclampsia (delivery <34 weeks), with a 1%, 5% and 10% false-positive rate for various combinations. The DR was higher for PlGF and PAPP-A than each alone. Similarly the DR was higher for MAP and PI than for each alone. Combining biochemical and biophysical markers increased detection further.

For direct observed risk distribution, the proportion of early pre-eclampsia cases with estimated early pre-eclampsia risk above the $99^{th}$, $95^{th}$ and $90^{th}$ centile in the appropriate population (all unaffected pregnancies or just controls) was calculated. Table 4 shows the proportions for risks calculated from different combinations of biochemical and biophysical markers, without considering prior risk. The results for biochemical markers alone are less predictive than the model predictions. For the biophysical markers alone and in combination with biochemical markers, the results were in line with predictions.

Table 5 shows the proportions of pre-eclampsia cases with high risk results based on prior risk factors alone. Table 6 shows the proportions with high risk of early pre-eclampsia based on prior risk factors as well as the biochemical and physical marker profile. Table 7 shows the proportion of late pre-eclampsia cases with high risk of late outcome; selected combinations only.

To summarize certain aspects, the background risk of pre-eclampsia for the pregnant individual is the incidence of pre-eclampsia in the population being screened (for example, the incidence of pre-eclampsia in pregnant women of the same ethnicity as the pregnant individual).

In certain instances, the MOM PlGF and/or the median value of PlGF obtained from a group of pregnant women with unaffected pregnancies is corrected for the gestational age of the fetus using the following formula: Gestational Age (GA) Corrected PlGF=277.908−6.97605*GA+0.0477151*GA*GA, where GA=gestational age in days. In certain instances, the MOM measured amount of PAPP-A and/or the median value of PAPP-A obtained from a group of pregnant women with unaffected pregnancies is corrected for the maternal weight of the pregnant individual using the following formula: Maternal Weight (WT) Corrected PAPP-A=−0.03239+69.3975/WT, where WT=weight of the pregnant woman in kilograms.

Biophysical markers were also examined. A total of 7658 women with unaffected pregnancies had uterine Doppler PI measurements and 6584 had mean arterial blood pressures (MAP). PI increased steadily with gestation and MAP reduced slightly, albeit reaching statistical significance. After expressing values in MoMs, PI declined slightly with increasing weight whilst MAP increased markedly. Both effects were stronger when BMI was used instead of weight, although not greatly so.

Median PI and MAP were increased in pre-eclampsia (Tables 21 & 22). Whilst the median increase in MAP did not appear great, the standard deviation was much less than PI ($\log_{in}$ values in unaffected pregnancies 0.035 and 0.12 respectively), and the effects were comparable.

Assuming multi-variate Gaussian fit and using the observed parameters for early pre-eclampsia and unaffected pregnancies, model predicted detection rates for fixed false-positive rates were estimated. Risks were also calculated for every case and control in order to estimate detection and false-positive rates directly. The rates were estimated for various combinations of the biochemical markers, biophysical markers and risk factors.

Thus, this example shows that in screening for pre-eclampsia, there was significant independent contributions from maternal factors, blood pressure (MAP), maternal blood PlGF and PAPP-A. Screening by a combination of PlGF and/or PAPP-A with MAP was estimated to identify about 70% of individuals developing early pre-eclampsia at a false positive rate of 10%. Addition of uterine artery PI to the screen was estimated to identify over 90% of individuals developing early pre-eclampsia at a false positive rate of 10%. Screening by a combination of PlGF, PAPP-A, and MAP was estimated to identify about 60% of individuals developing late pre-eclampsia at a false positive rate of 10%.

TABLE 1

Comparison of current LRs with those in Papageorghiou et al

| Factor | Value | Current | Papageorghiou |
|---|---|---|---|
| Race | Black | 2.18 | 1.45 |
|  |  | 0.57 | 0.90 |
| Smoker | Yes | 0.56 | 0.51 |
|  | No | 1.04 | 1.10 |
| Parity | 0 | 1.34 | 1.23 |
|  | 1 | 0.66 | 0.72 |
|  | 2 | 0.63 | 1.72 |
|  | 3+ | 1.14 | 2.07 |
| BMI | <25 | 0.65 | 0.82 |
|  | 25-34 | 1.23 | 1.08 |
|  | 35+ | 3.05 | 2.18 |
| Hypertensive | Yes | 10.24 | 12.52 |
|  | No | 0.94 | 0.95 |
| Hx PE (parity 1+) | Yes | 7.87 | 3.19 |
|  | No | 0.64 | 0.81 |
| Mother/sister PE* | Yes | 2.89 | 2.49 |
|  | No | 0.92 | 0.97 |

Current = mother;
Papageorghiou = sister

TABLE 2

Distribution of risk factors, according to gestation of delivery

| Factor | Value | <34 weeks | 34-6 weeks | 37+ weeks |
|---|---|---|---|---|
| Race | Black | 38% | 45% | 42% |
|  | Other | 62% | 55% | 58% |
| Smoker | Yes | 0.0% | 9.1% | 5.2% |
|  | No | 100% | 91% | 95% |
| Parity | 0 | 52% | 59% | 66% |
|  | 1 | 24% | 32% | 21% |
|  | 2 | 10% | 5% | 8% |
|  | 3+ | 14% | 5% | 5% |
| BMI | <25 | 38% | 32% | 36% |
|  | 25-34 | 59% | 55% | 44% |
|  | 35+ | 3% | 14% | 19% |
| Hypertensive | Yes | 14% | 9% | 3% |
|  | No | 86% | 91% | 97% |
| Hx PE (parity 1+) | Yes | 50% | 67% | 65% |
|  | No | 50% | 33% | 35% |

TABLE 2-continued

Distribution of risk factors, according to gestation of delivery

| Factor | Value | <34 weeks | 34-6 weeks | 37+ weeks |
|---|---|---|---|---|
| Mother/sister PE* | Yes | 10% | 18% | 10% |
| | No | 90% | 82% | 90% |

*Cunent = mother;
Papageorghiou = sister

TABLE 3

Early pre-eclampsia: model predicted detection rates for fixed FPRs

| Combination | 1% FPR | 5% FPR | 10% FPR |
|---|---|---|---|
| PlGF | 23% | 37% | 46% |
| PAPP-A | 19% | 36% | 46% |
| PP13 | 4% | 13% | 22% |
| MAP | 26% | 44% | 55% |
| PI | 28% | 50% | 62% |
| PlGF & PAPP-A (Double) | 30% | 47% | 57% |
| PlGF, PAPP-A & PP13 (Triple) | 30% | 48% | 57% |
| MAP & PI | 51% | 77% | 87% |
| PlGF & MAP | 38% | 56% | 66% |
| PAPP-A & MAP | 38% | 63% | 74% |
| Double & MAP | 45% | 67% | 77% |
| Triple & MAP | 46% | 67% | 77% |
| PlGF, MAP & PI | 61% | 84% | 91% |
| PAPP-A, MAP & PI | 60% | 84% | 91% |
| Double, MAP & PI | 67% | 87% | 93% |
| Triple, MAP & PI | 67% | 87% | 94% |

TABLE 4

Early pre-eclampsia risk (without prior factors): proportion of cases above fixed normal centiles

| Combination | $99^{th}$ | 95th | 90th |
|---|---|---|---|
| PlGF | 10% | 31% | 41% |
| PAPP-A | 21% | 24% | 41% |
| PP13 | 3% | 17% | 17% |
| MAP | 28% | 44% | 56% |
| PI | 14% | 52% | 69% |
| PlGF & PAPP-A (Double) | 17% | 38% | 48% |
| PlGF, PAPP-A & PP13 (Triple) | 17% | 41% | 48% |
| MAP & PI | 28% | 84% | 88% |
| PlGF & MAP | 44% | 48% | 68% |
| PAPP-A & MAP | 44% | 56% | 68% |
| Double & MAP | 48% | 56% | 64% |
| Triple & MAP | 48% | 56% | 68% |
| PlGF, MAP & PI | 52% | 76% | 92% |
| PAPP-A, MAP & PI | 36% | 80% | 92% |
| Double, MAP & PI | 56% | 72% | 96% |
| Triple, MAP & PI | 52% | 80% | 96% |

TABLE 5

Early pre-eclampsia risk (prior factors only): proportion of cases above fixed normal centiles

| Type of pre-eclampsia | 99th | 95th | $90^{th}$ |
|---|---|---|---|
| Early | 21% | 41% | 59% |
| Other | 10% | 32% | 57% |
| All | 12% | 34% | 57% |

TABLE 6

Early pre-eclampsia risk (with prior factors): proportion of early cases above fixed normal centiles

| Combination | 99th | 95th | $90^{th}$ |
|---|---|---|---|
| PlGF | 28% | 45% | 62% |
| PAPP-A | 34% | 52% | 62% |
| PP13 | 24% | 41% | 45% |
| MAP | 36% | 48% | 68% |
| PI | 24% | 66% | 72% |
| Double | 24% | 59% | 66% |
| Triple | 31% | 59% | 69% |
| MAP & PI | 44% | 76% | 88% |
| PlGF & MAP | 40% | 64% | 68% |
| PAPP-A & MAP | 40% | 60% | 76% |
| Double & MAP | 48% | 68% | 72% |
| Triple & MAP | 48% | 68% | 72% |
| PlGF, MAP & PI | 56% | 80% | 92% |
| PAPP-A, MAP & PI | 52% | 84% | 92% |
| Double, MAP & PI | 60% | 88% | 96% |
| Triple, MAP & PI | 60% | 88% | 96% |

TABLE 7

Late pre-eclampsia risk (with prior factors): proportion of late cases above fixed normal centiles

| Combination | 99th | 95th | 90th |
|---|---|---|---|
| PlGF | 7% | 31% | 45% |
| PAPP-A | 6% | 27% | 42% |
| MAP | 18% | 37% | 56% |
| PI | 6% | 32% | 44% |
| Double | 9% | 30% | 42% |
| MAP & PI | 19% | 40% | 57% |
| Double & MAP | 17% | 34% | 58% |
| Double, MAP & PI | 19% | 43% | 52% |

TABLE 21

Median MoM (#) for each biophysical marker according to outcome

| Marker | Controls | FGR | PET | PIH | Preterm |
|---|---|---|---|---|---|
| PI | 1.00 (7658) | 1.08 (296) | 1.31 (128) | 1.07 (89) | 1.06 (58) |
| MAP | 1.00 (6584) | 1.14 (296) | 1.09 (120) | 1.18 (82) | 1.12 (56) |

TABLE 22

Pre-eclampsia: median MoM, according to gestation of delivery

| Marker | <34 weeks # = 25 | 34-36 # = 21 | 37+ # = 74 |
|---|---|---|---|
| PI | 1.58 | 1.48 | 1.12 |
| MAP | 1.12 | 1.11 | 1.08 |

TABLE 23

Correlations with PI

| Marker | Pre-eclampsia | Unaffected |
|---|---|---|
| PlGF | −0.25** | −0.07 |
| PP13 (Delfia) | −0.41** | −0.09* |
| PAPP-A | −0.28** | −0.17** |
| MAP | −0.12 | −0.08** |

*significant;
**highly significant

TABLE 24

Correlations with MAP

| Marker | Pre-eclampsia | Unaffected |
|---|---|---|
| PlGF | 0.06 | −0.04 |
| PP13 (Delfia) | 0.06 | −0.01 |
| PAPP-A | 0.07 | 0.00 |

*significant;
**highly significant

Example 2

Clinical Study of the Role of Multiple Biochemical and Biophysical Markers for Detecting Pre-Eclampsia and Related Placental Disorders This example shows the usefulness of various combinations of biochemical markers for determining risk of pre-eclampsia and related disorders in a pregnant individual. In particular, the biochemical markers MMP3, PlGF, TNFR1, and PP13 (PerkinElmer DELFIA assay format) were found to have statistical significance for predicting pre-eclampsia and related disorders. One or more of markers demonstrated to have predictive power for detecting pre-eclampsia can be used in combination with marker sets described herein, such as PlGF and/or PAPP-A and MAP.

A study was undertaken to screen for adverse pregnancy outcomes in women attending for routine assessment of risk for chromosomal abnormalities. Maternal characteristics and medical history were recorded and blood collected. Serum was stored at −80° C. for subsequent biochemical analysis. Written informed consent was obtained from the women agreeing to participate in the study, which was approved by King's College Hospital Ethics Committee. Additional information concerning clinical population and sample collection is provided in Example 3.

Firstly, parameters that affect amounts of biochemical markers in a maternal biological sample were identified. It was observed that (1) PlGF and ADAM12 increased steeply with gestation. None of the other markers were statistically significantly associated with gestation and the overall median was used for MoMing; (2) TNFR1 MoMs increase with weight, (3) PP13 & ADAM12 decreased with weight; (4) MMP3 & PlGF were unrelated to weight. Inverse weight regression equations were used for adjustment; BMI was no better a covariable than weight.

For detecting individuals having pre-eclampsia, the results were statistically significant (2-tail) for MMP3 (P<0.005), PlGF (P<0.0001), TNFR1 (P<0.05) and PP13 Delfia (P<0.02). Table 8 shows median MoM values for unaffected pregnancies (Control), fetal growth restriction (FGR), pre-eclamptic (PET), pregnancy induced hypertension (PIH), and preterm pregnancies. Table 9 shows the $10^{th}$ and $90^{th}$ centile MoMs in controls, and standard deviations. The data shows that TNFR1 had a very tight normal distribution. For PP13, on the basis of data so far, ELISA immunoassay had more than double the SD of DELFIA immunoassay.

Figure 4:
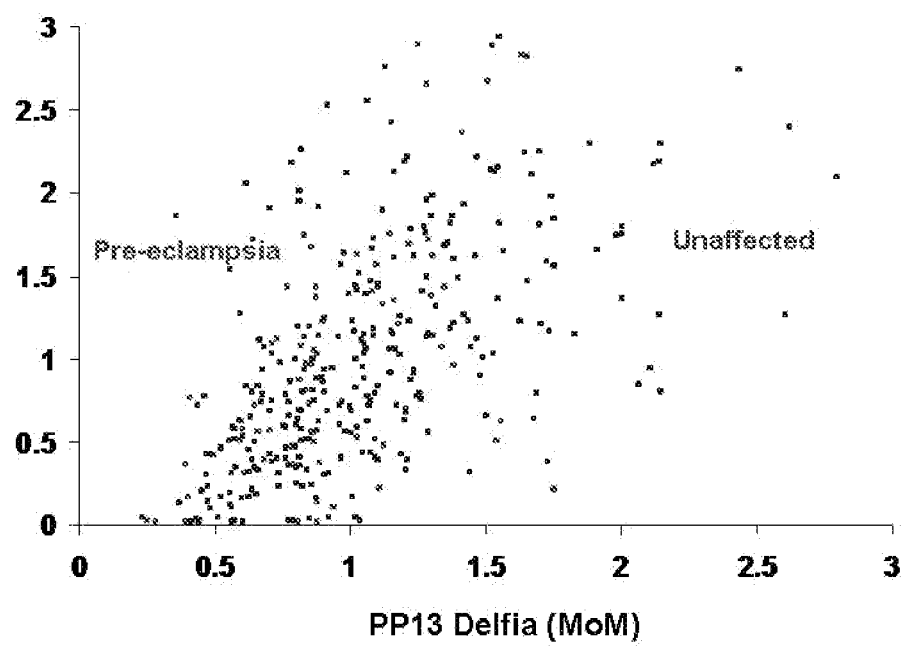
FIG. 4 is a scatter plot depicting the correlation between PP13 measured using an ELISA immunoassay and a PerkinElmer DELFIA immunoassay in pre-eclamptic and unaffected groups.

FIG. 4 shows the paired PP13 Delfia and ELISA MoMs for pre-eclampsia and unaffected pregnancies. This demonstrates that the PerkinElmer DELFIA immunoassay had less deviation relative to the ELISA technology employed in this experiment.

PlGF was found to be the strongest biochemical marker in the <34 weeks pre-eclampia group, followed by PP13 (Pre-eclampsia: median MoM according to severity (Table 10).

These and other biochemical markers were also useful for detecting pre-eclampsia amongst the 34-36 weeks group and 37+ weeks group.

Figure 5:
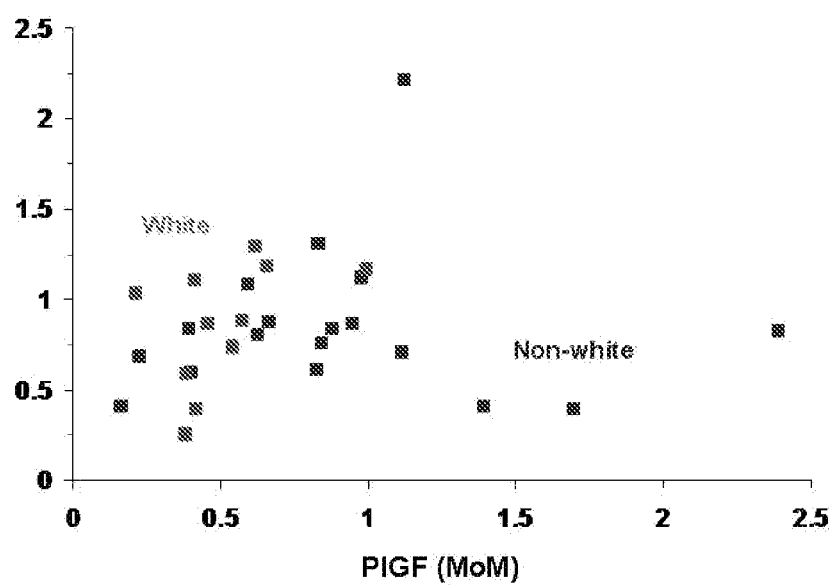
FIG. 5 is a scatter plot depicting correlation between PlGF and PP13 in early pre-eclampsia in Caucasian woman and non-Caucasian women.
Figure 6:
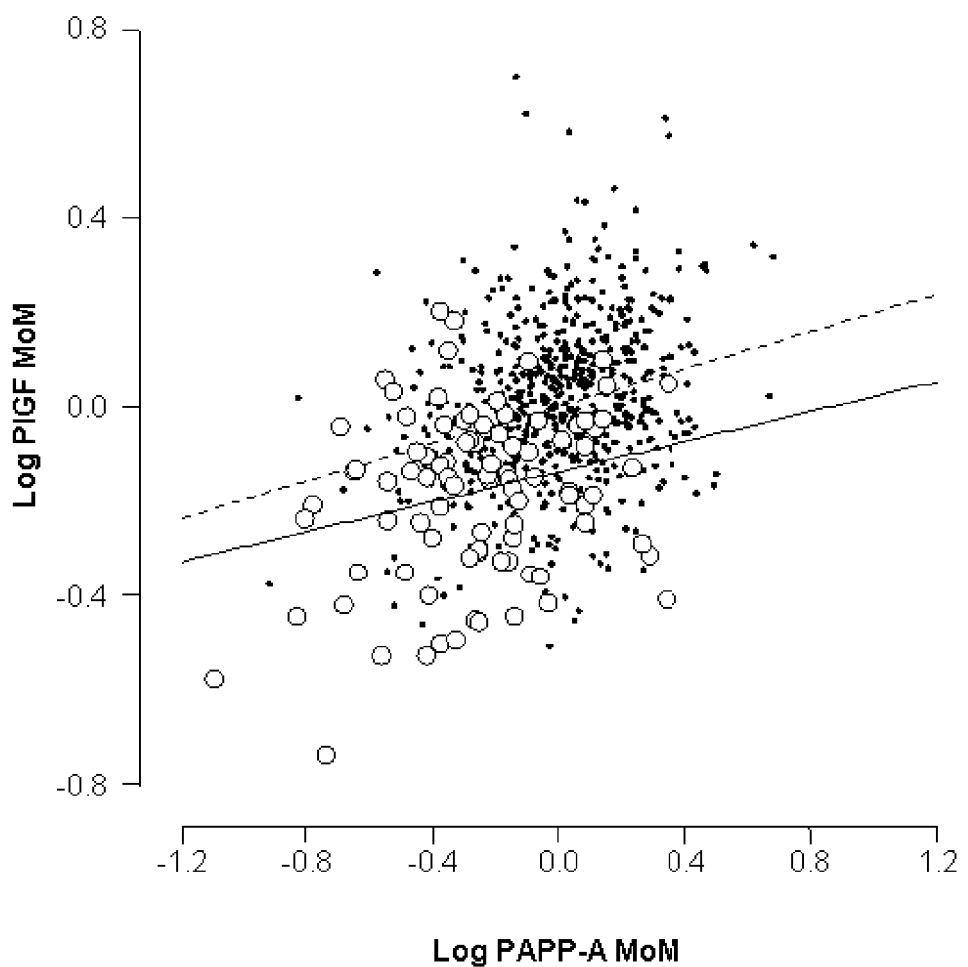
FIG. 6 is a scatter plot depicting the relationship between log placental growth factor (PlGF) MoM and log pregnancy associated plasma protein A (PAPP-A) MoM in euploid (solid dots and dashed regression line) and trisomy 21 pregnancies (open circles and solid regression line), which shows a correlation between PlGF and PAPP-A in both unaffected pregnant individuals and those having pre-eclampsia.

The effect of ethnicity on the biochemical marker MoMs was examined (see Table 11). The results showed that there was a strong effect of ethnicity on MMP3, PlGF and possibly PP13 ELISA. In addition, the effect of smoking on the biochemical marker MoMs was examined (see Table 12). The results showed an effect of smoking on PlGF, PP13 and ADAM12. The effect of parity and maternal age also was examined. None of the biochemical markers was markedly related to parity or maternal age, although there appeared to be a small steady increase in PP13. There were only 16 ART pregnancies but it is noteworthy that the median for PlGF was 0.87 MoM. The relevant centiles for unaffected pregnancies are shown in Table 13. Table 14 shows centiles in cases with early pre-eclampsia. PlGF was the best predictor at the $10^{th}$ percentile, followed by PP13. Table 15 shows centiles in pre-eclamptic cases delivering at 34-36 weeks. There was no material correlation between PlGF and PP13 (performing using PerkinElmer DELFIA immunoassay) in unaffected pregnancies (Table 16), but there appears to be a small correlation in pre-eclampsia (Table 17). FIG. 5 shows the paired MoMs for the 29 early pre-eclampsia cases.

The median ($\log_{10}$ SD) PAPP-A amount in pre-eclampsia and unaffected control pregnancies was 0.79 MoM (0.22) and 1.08 MoM (0.22) respectively. It was also highly correlated with both PlGF and PP13 (Table 18). The extent of PAPP-A reduction was greater in the early pre-eclampsia pregnancies with median 0.54 MoM. Free beta hCG was not a marker of pre-eclampsia (medians 1.16 and 1.10 in pre-eclampsia and unaffected pregnancies) and shows weaker correlation with PlGF and PP13 (Table 19). The median ($\log_{10}$ SD) screening marker amounts in the entire series of 7413 unaffected pregnancies—not just controls was 1.02 MoM (0.24) for PAPP-A and 1.09 MoM (0.26) free beta hCG.

The reductions in median amounts of PP13 ELISA, PP13 Delfia and ADAM12 (see Table 8) were statistically significant (all P<0.0001). There was a relatively high rate of smoking in the growth restriction group, but the effect was still apparent after stratification (see e.g., Table 20 compared with Table 12). The median PAPP-A amount was also reduced (0.80 MoM).

Thus, this example shows that in detecting pre-eclampsia, PlGF, PP13, TNFR1 were the more effective markers; in detecting fetal growth restriction, PlGF, PP13, ADAM12 and MMP3 were the more effective markers; in detecting pregnancy induced hypertension (also known as gestational hypertension), PP13, PlGF and MMP3 were the more effective markers, and in detecting preterm labour, PP13, PlGF and MMP3 were the more effective markers. Also shown is that PlGF, PP13 and other markers are useful for detecting pre-eclampsia throughout pregnancy, including <34 weeks (inclusive) and later.

TABLE 8

Median MoM (#) for each biochemical marker according to outcome

| Marker | Controls | FGR | PET | PIH | Preterm |
|---|---|---|---|---|---|
| MMP3 | 1.00 (572) | 1.07 (296) | 1.17 (128) | 1.10 (88) | 1.18 (57) |
| PlGF | 1.00 (571) | 0.96 (296) | 0.84 (127) | 0.89 (88) | 1.10 (57) |
| TNFR1 | 0.99 (572) | 1.01 (296) | 1.06 (128) | 1.01 (88) | 1.04 (57) |
| PP13 (ELISA) | 1.00 (312) | 0.68 (170) | 0.97 (77) | 0.70 (48) | 0.90 (21) |
| PP13 (Delfia) | 1.00 (570) | 0.80 (296) | 0.87 (128) | 0.92 (88) | 0.83 (58) |
| ADAM12 | 0.99 (572) | 0.84 (296) | 0.98 (128) | 0.99 (88) | 1.02 (58) |

TABLE 9

10th & 90th centile MoMs in controls, and SD, assuming $\log_{10}$ Gaussian fit

| Marker | 10th centile | 90th centile | SD |
|---|---|---|---|
| MMP3 | 0.55 | 1.82 | 0.20 |
| PlGF | 0.62 | 1.86 | 0.19 |
| TNFR1 | 0.78 | 1.26 | 0.08 |
| PP13 (ELISA) | 0.23 | 2.74 | 0.42 |
| PP13 (Delfia) | 0.58 | 1.71 | 0.18 |
| ADAM12 | 0.68 | 1.42 | 0.12 |

TABLE 10

Pre-eclampsia: median MoM, according to gestation of delivery

| Marker | < 34 weeks # = 29 | 34-36 weeks # = 22 | 37+ weeks # = 77 |
|---|---|---|---|
| MMP3 | 1.12 | 1.21 | 1.16 |
| PlGF | 0.63 | 0.74** | 0.95 |
| TNFR1 | 1.09 | 1.07 | 1.03 |
| PP13 (ELISA)* | 1.02 | 0.55 | 1.05 |
| PP13 (Delfia) | 0.84 | 0.70 | 0.91 |
| ADAM12 | 1.07 | 0.84 | 0.99 |

*# = 24, 12 & 41;
**# = 21

TABLE 11

Unaffected pregnancies: median MoM according to ethnicity; proportions in parentheses

| Marker | Caucasian (72%) | African American (17%) | Indian (5%) | Chinese (2%) | Mixed (4%) | Non-Caucasian |
|---|---|---|---|---|---|---|
| MMP3 | 1.03 | 0.86 | 0.81 | 1.06 | 1.06 | 0.91 |
| PlGF | 0.94 | 1.43 | 1.18 | 0.98 | 1.06 | 1.27 |
| TNFR1 | 1.00 | 0.95 | 0.93 | 1.01 | 1.08 | 0.97 |
| PP13 (ELISA) | 0.92 | 1.24 | 0.79 | 1.11 | 1.19 | 1.15 |
| PP13 (Delfia) | 0.99 | 1.09 | 1.05 | 0.95 | 0.96 | 1.05 |
| ADAM12 | 0.97 | 1.09 | 0.92 | 1.10 | 1.05 | 1.05 |

TABLE 12

Unaffected pregnancies: median MoM according to smoking status; proportions in parentheses

| Marker | Non-smoker (96%) | Smoker (4%) |
|---|---|---|
| MMP3 | 0.99 | 1.04 |
| PlGF | 0.98 | 1.33 |
| TNFR1 | 0.99 | 1.08 |
| PP13 ELISA | 1.03 | 0.41 |
| PP13 Delfia | 1.02 | 0.54 |
| ADAM12 | 1.01 | 0.82 |

TABLE 13

Unaffected pregnancies: selected centiles (MoM)

| Marker | <1st | <5th | <10th | >90th | >95th | >99th |
|---|---|---|---|---|---|---|
| MMP3 | 0.29 | 0.45 | 0.55 | 1.82 | 2.30 | 3.25 |
| Caucasian | 0.26 | 0.48 | 0.56 | 1.99 | 2.59 | 3.36 |
| Non-Caucasian | 0.31 | 0.41 | 0.48 | 1.71 | 1.84 | 2.38 |
| PlGF | 0.39 | 0.50 | 0.62 | 1.86 | 2.19 | 3.78 |
| Non-Smoker | 0.40 | 0.50 | 0.62 | 1.84 | 2.15 | 3.68 |
| Smoker | 0.71 | 0.78 | 0.88 | 2.64 | 2.76 | 4.49 |
| Caucasian | 0.39 | 0.50 | 0.61 | 1.57 | 1.88 | 2.64 |
| Non-Caucasian | 0.42 | 0.54 | 0.71 | 2.33 | 2.75 | 4.51 |
| TNFR1 | 0.63 | 0.70 | 0.78 | 1.26 | 1.34 | 1.60 |
| PP13 (ELISA) | 0.02 | 0.04 | 0.22 | 2.66 | 4.10 | 7.92 |
| Non-Smoker | 0.02 | 0.10 | 0.25 | 2.56 | 3.87 | 7.76 |
| PP13 (Delfia) | 0.40 | 0.49 | 0.58 | 1.72 | 2.02 | 2.75 |
| Non-Smoker | 0.41 | 0.54 | 0.60 | 1.72 | 2.02 | 2.62 |
| Smoker | 0.24 | 0.30 | 0.32 | 0.96 | 1.13 | 1.15 |
| ADAM12 | 0.43 | 0.58 | 0.67 | 1.41 | 1.56 | 2.00 |
| Non-Smoker | 0.45 | 0.57 | 0.68 | 1.42 | 1.57 | 1.92 |
| Smoker | 0.63 | 0.64 | 0.65 | 1.29 | 1.34 | 1.98 |

TABLE 14

Early pre-eclampsia: cases in relation to selected centiles

| Marker | # | <1st | <5th | <10th | >90th | >95th | >99th |
|---|---|---|---|---|---|---|---|
| MMP3 | 29 | 1 | 1 | 2 | 4 | 0 | 0 |
| PlGF | 29 | 7 | 10 | 15 | 1 | 0 | 0 |
| TNFR1 | 29 | 1 | 2 | 5 | 5 | 3 | 0 |
| PP13 ELISA | 24 | 2 | 3 | 5 | 4 | 3 | 1 |
| PP13 Delfia | 29 | 5 | 5 | 7 | 1 | 1 | 0 |
| ADAM12 | 29 | 2 | 2 | 6 | 2 | 0 | 0 |

TABLE 15

Pre-eclampsia delivering 34-36 weeks: cases in relation to selected centiles

| Marker | # | <1st | <5th | <10th | >90th | >95th | >99th |
|---|---|---|---|---|---|---|---|
| MMP3 | 22 | 0 | 1 | 2 | 4 | 3 | 1 |
| PlGF | 21 | 3 | 5 | 7 | 1 | 0 | 0 |
| TNFR1 | 22 | 1 | 1 | 3 | 5 | 4 | 0 |
| PP13 (ELISA) | 12 | 2 | 3 | 3 | 0 | 0 | 0 |
| PP13 (Delfia) | 22 | 2 | 3 | 8 | 0 | 0 | 0 |
| ADAM12 | 22 | 1 | 4 | 5 | 1 | 1 | 0 |

TABLE 16

Correlations in unaffected pregnancies (excluding outliers)

| Marker | MMP3 | PlGF | TNFR1 | PP13ELISA | PP13Delfia |
|---|---|---|---|---|---|
| PlGF | 0.02 | — | | | |
| TNFR1 | 0.47** | 0.09* | — | | |
| PP13 (ELISA) | −0.14* | 0.03 | −0.06 | — | |
| PP13 (Delfia) | −0.15** | 0.05 | 0.03 | 0.56** | — |
| ADAM12 | −0.08 | 0.27** | −0.03 | 0.31** | 0.38** |

*significant;
**highly significant

TABLE 17

Correlations in pre-eclampsia (excluding outliers)

| Marker | MMP3 | PlGF | TNFR1 | PP13 (ELISA) | PP13 (Delfia) |
|---|---|---|---|---|---|
| PlGF | −0.01 | — | | | |
| TNFR1 | 0.51** | 0.04 | — | | |
| PP13 (ELISA) | 0.15 | 0.13 | −0.10 | — | |
| PP13 (Delfia) | −0.02 | 0.24* | −0.06 | 0.48** | — |
| ADAM12 | −0.04 | 0.16 | −0.25* | 0.44** | 0.43** |

TABLE 18

Correlations with PAPP-A (excluding outliers)

| Marker | Pre-eclampsia | Unaffected |
|---|---|---|
| MMP3 | 0.12 | −0.07 |
| PlGF | 0.34** | 0.27** |
| TNFR1 | −0.02 | −0.04 |
| PP13 (ELISA) | 0.11 | 0.20** |
| PP13 (Delfia) | 0.38** | 0.27** |
| ADAM12 | 0.49** | 0.42** |

*significant;
**highly significant

TABLE 19

Correlations with free beta hCG (excluding outliers)

| Marker | Pre-eclampsia | Unaffected |
|---|---|---|
| MMP3 | 0.02 | −0.06 |
| PlGF | 0.08 | 0.18** |
| TNFR1 | 0.05 | 0.10* |
| PP13 (ELISA) | 0.26* | 0.15* |
| PP13 (Delfia) | 0.40** | 0.32** |
| ADAM12 | 0.26** | 0.21** |

*significant; **highly significant

TABLE 20

Fetal growth restriction: median MoM, according to smoking status; proportions in parentheses

| Marker | Non-smoker (82%) | Smoker (18%) |
|---|---|---|
| MMP3 | 1.04 | 1.24 |
| PlGF | 0.90 | 1.16 |
| TNFR1 | 1.01 | 1.13 |
| PP13 ELISA | 0.79 | 0.13 |
| PP13 Delfia | 0.86 | 0.52 |
| ADAM12 | 0.88 | 0.71 |

Example 3

Clinical Study of the Role of Biochemical Markers and Doppler Biophysical Markers for Detecting Maternal Hypertensive Disorders This example shows the usefulness of various combinations of biochemical and biophysical markers, including PlGF, PAPP-A, uterine artery PI, for determining risk that a pregnant individual is carrying a fetus having a chromosomal abnormality.

A study was undertaken to screen for adverse pregnancy outcomes in women attending for routine assessment of risk for chromosomal abnormalities by measurement of fetal nuchal translucency thickness and maternal serum PAPP-A and free beta-hCG at $11^{+0}$-$13^{+6}$ weeks of gestation. Maternal characteristics and medical history were recorded, and the uterine artery PI by transabdominal color Doppler were measured and stored serum at −80° C. for subsequent biochemical analysis. Written informed consent was obtained from the women agreeing to participate in the study, which was approved by King's College Hospital Ethics Committee.

The case-control study population comprised of 127 pregnancies that subsequently developed PE, including 29 that required delivery before 34 weeks and 98 with late-PE, 88 with gestational hypertension (GH), 296 cases that delivered small for gestational age (SGA) neonates, 57 cases with spontaneous preterm delivery before 34 weeks and 41 cases of trisomy 21. Each case was matched with one control case that had blood collected and stored on the same day that did not develop any pregnancy complications and resulted in the live birth of phenotypically normal neonates.

Individuals were asked to complete a questionnaire on maternal age, racial origin (Caucasian, African American, Indian, Pakistani, Chinese or Japanese and Mixed), cigarette smoking during pregnancy (yes or no), method of conception (spontaneous, use of ovulation drugs and in-vitro fertilization), medical history (including chronic hypertension, diabetes mellitus, anti-phospholipid syndrome, thrombophilia, human immunodeficiency virus infection, and sickle cell disease), medication (including anti-hypertensive, anti-depressant, anti-epileptic, anti-inflammatory, anti-thyroid, aspirin, β-mimetic, insulin, steroids, thyroxin), parity (parous or nulliparous if no delivery beyond 23 weeks), obstetric history (including previous pregnancy with PE) and family history of PE (mother). The maternal weight and height were measured and the body mass index (BMI) was calculated in $Kg/m^2$.

Duplicate serum samples of 100 μL was used to measure PlGF concentration by a quantitative enzyme linked immunoassay (ELISA) technique using Quantikine® human PlGF immunoassay (R&D systems Europe Ltd., Abingdon, UK). The assays were performed on an automated ELISA processor (Dade-Behring BEP 2000, Liederbach, Germany). Absorbance readings were taken on a VICTOR™ plate reader (PerkinElmer Life and Analytical Sciences, Turku, Finland) and PlGF concentrations were determined using MultiCalc software (PerkinElmer Life and Analytical Sciences, Turku, Finland). The lower limit of detection of the assay was 7 pg/mL and the between-batch imprecision was 8.3% at a PlGF concentration of 48 pg/mL, 5.6% at 342 pg/mL and 5.1% at 722 pg/mL. Samples whose coefficient of variation of the duplicates exceeded 15% were reanalyzed.

The measured concentration of PlGF was log transformed to make the distribution Gaussian. Multiple regression analysis was then used to determine which of the factors amongst the maternal characteristics and fetal crown-rump length (CRL) were significant predictors of log PlGF in the control group and from the regression model the value in each case and control was expressed as a multiple of the expected median in the control group (MoM). A Box-whisker plot of PlGF MoM of each outcome group was created. A Mann-Whitney test was used to determine the significance of differences in the median MoM in each outcome group to that in the controls.

In each case and control, the measured PAPP-A and uterine artery PI were converted into MoMs after adjustment for gestation, maternal age, ethnicity, BMI or weight, parity, previous history of PE and method of conception (see, for example Kagen et al., *Ultrasound Obstet Gynecol* 31:493-502 (2008)) Regression analysis was then used to determine the significance of association between log PlGF MoM with log PAPP-A MoM, log uterine artery PI MoM, birth weight percentile and gestation at delivery in each outcome group.

Logistic regression analysis was used to determine which of the factors amongst the maternal characteristics, log PlGF MoM, log PAPP-A MoM and log uterine artery PI MoM had a significant contribution in predicting PE. The performance of screening was determined by receiver operating characteristic (ROC) curves. The statistical software package SPSS 15.0 (SPSS Inc., Chicago, Ill.) was used for all data analyses.

The maternal characteristics of each of the outcome groups are compared in Table 30.

Multiple regression analysis in the control group demonstrated that for log PlGF significant independent contributions were provided by fetal CRL, maternal weight, cigarette smoking and ethnic origin: log expected PlGF=1.150+0.008× CRL in mm−0.002×weight in Kg+(0.199 if smoking, 0 if not)+(0.177 if Black, 0.100 if Indian or Pakistani, 0 if other ethnic origins); $R^2=0.237$, $p<0.0001$. This formula was used for each individual to derive the expected log PlGF and then expressed the observed value as a MoM of the expected (FIG. 1, Table 30).

Figure 2A:
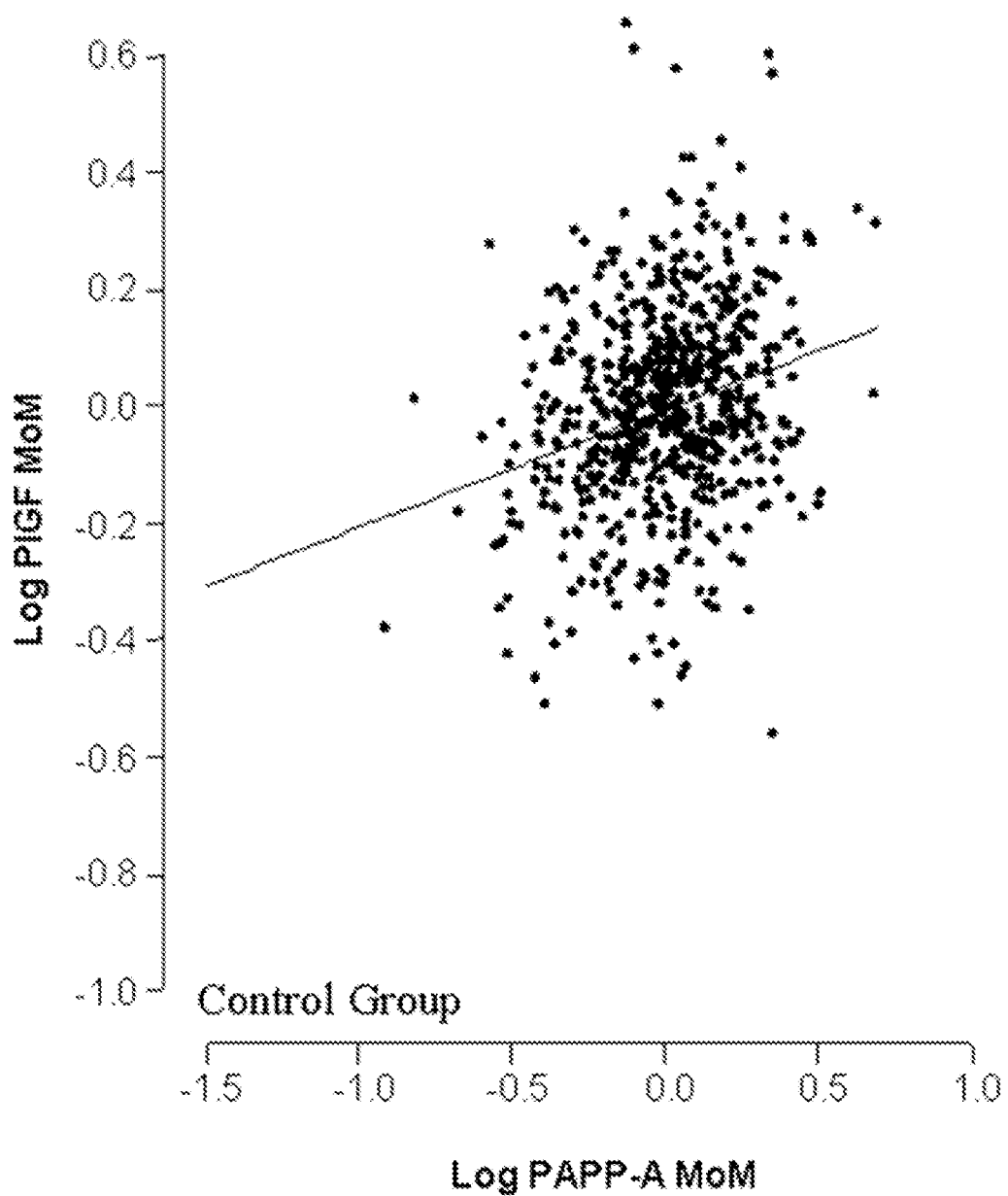
FIG. 2 is a pair of scatter plots depicting the relationship between log placental growth factor (PlGF) MoM and log PAPP-A MoM in a control group (A) and a pre-eclampsia group (B), which shows a modest correlation between amounts of PlGF and PAPP-A in both unaffected pregnant individuals and those having pre-eclampsia.
Figure 2B:
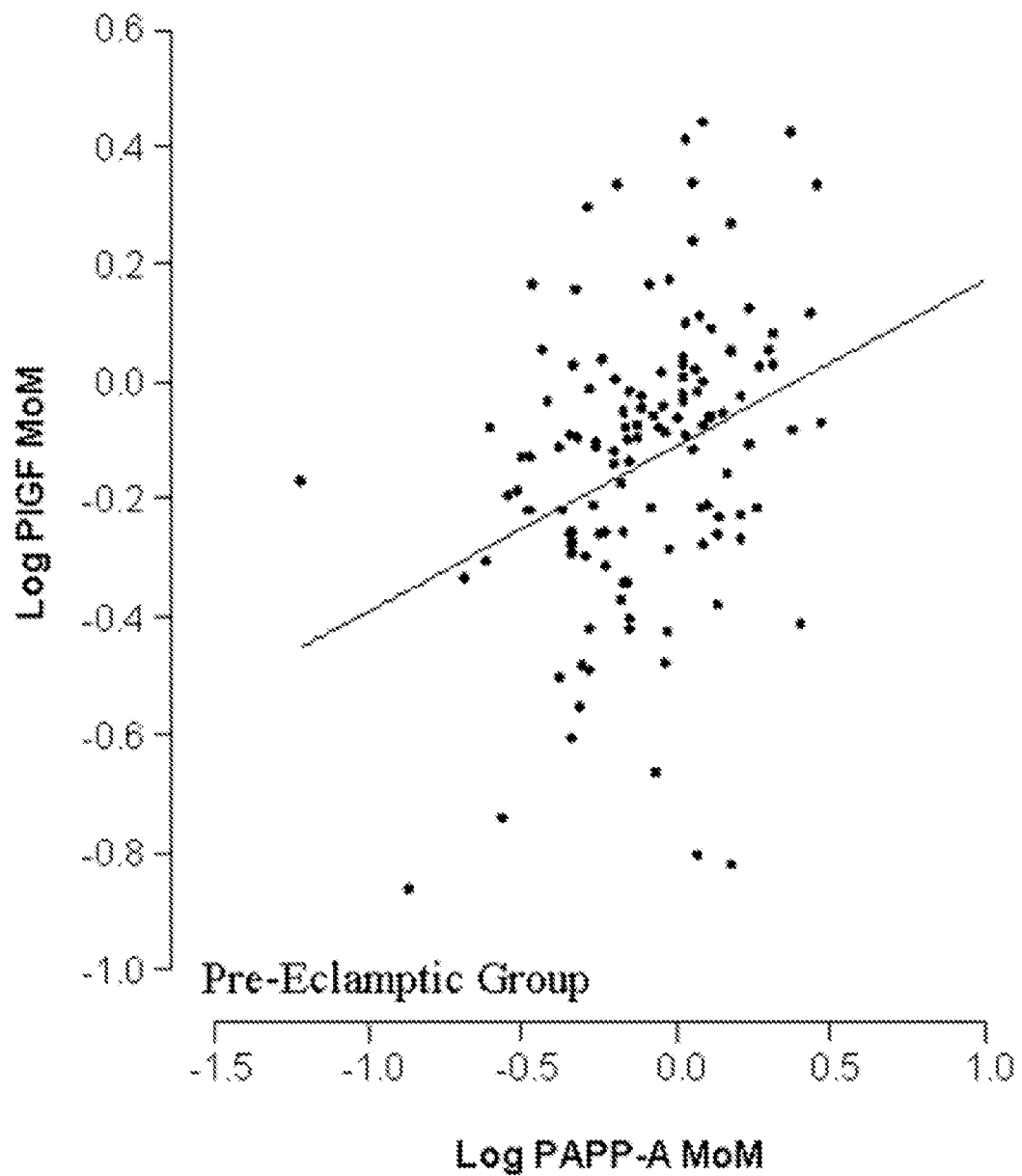
Figure 3A:
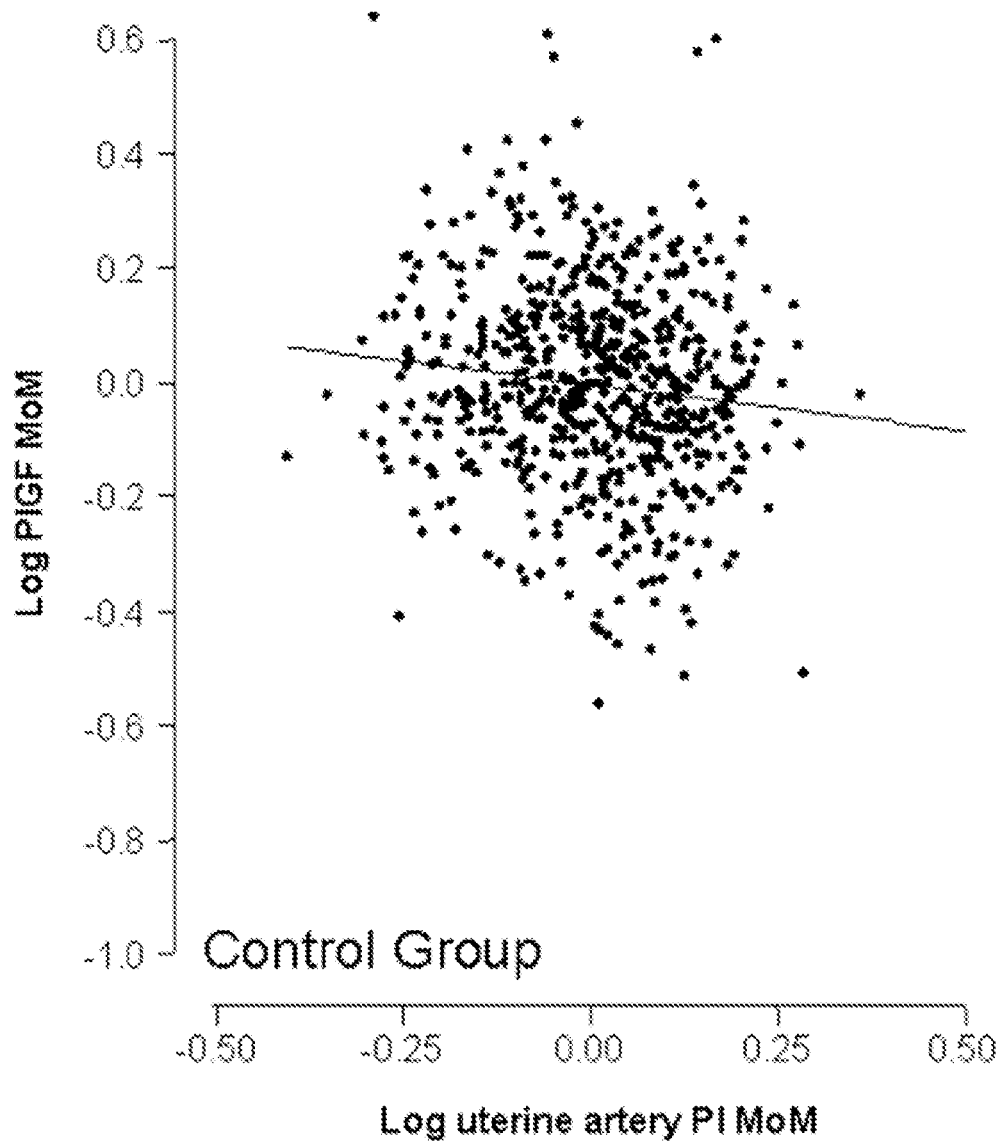
FIG. 3 is a pair of scatter plots depicting the relationship between log placental growth factor (PlGF) MoM and log uterine artery PI MoM in a control group (A) and a pre-eclamptic group (B), which shows a negative correlation between PlGF and PI.
Figure 3B:
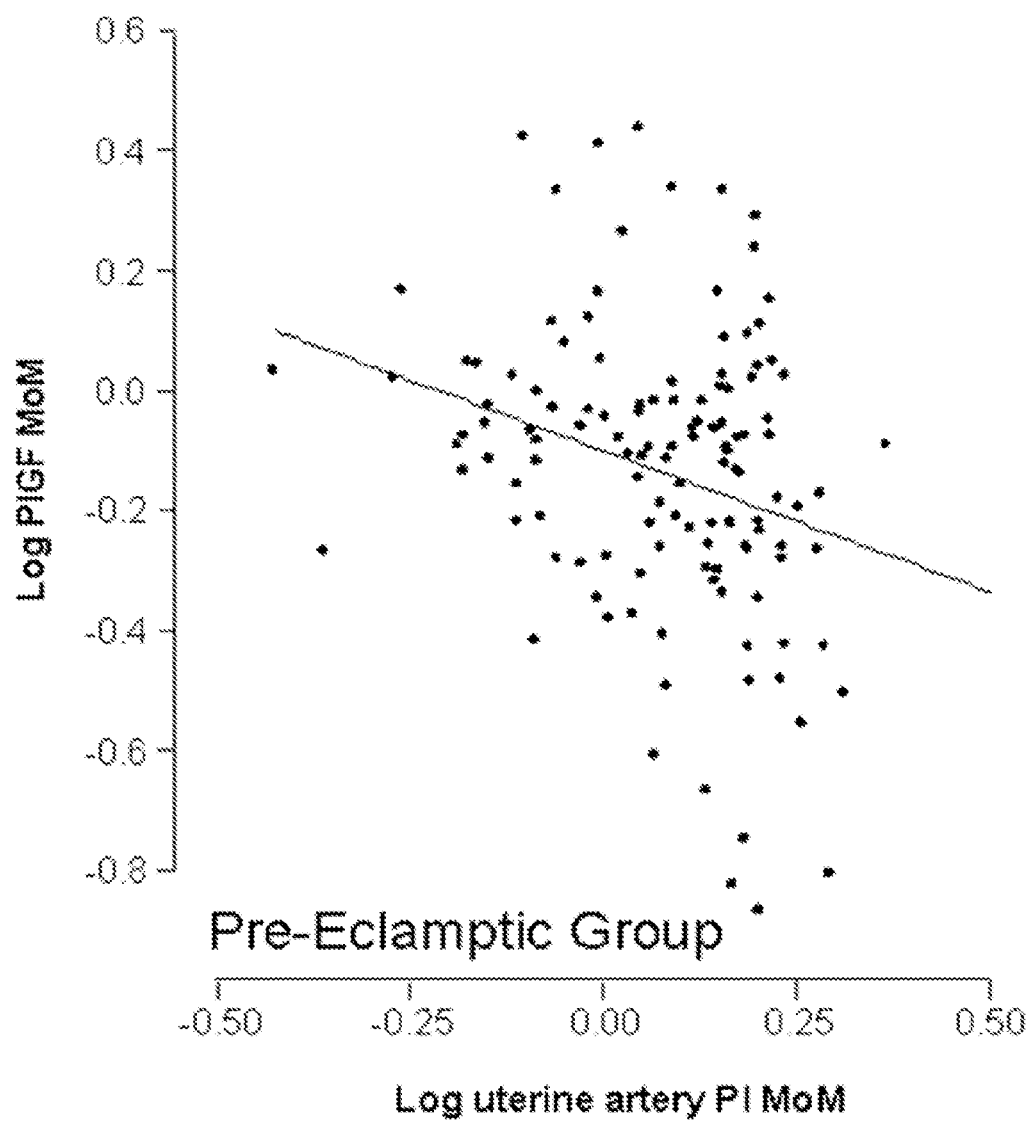

There was a significant association between log PlGF MoM and log PAPP-A MoM ($r=0.264$, $p<0.0001$; FIG. 2), log uterine artery PI MoM ($r=0.102$, $p=0.012$; FIG. 3), birth weight percentile ($r=0.114$, $p=0.005$) but not gestational age at delivery ($p=0.960$).

In both the early-PE and late-PE groups, PlGF and PAPP-A were lower and uterine artery PI was higher than in the controls (FIG. 1, Table 30). There was a significant association between log PlGF MoM and log PAPP-A MoM ($r=0.325$, $p<0.0001$; FIG. 2), log uterine artery PI MoM ($r=0.279$, $p=0.001$; FIG. 3), gestational age at delivery ($r=0.256$, $p=0.004$) and birth weight percentile ($r=0.338$, $p<0.0001$).

Logistic regression analysis demonstrated that significant contributions for the detection of early-PE were provided from maternal factors, PlGF, PAPP-A and uterine artery PI ($R^2=0.500$, $p<0.0001$, Table 31). Logistic regression analysis demonstrated that significant contributions for the detection of late-PE were provided from maternal factors, PlGF and uterine artery PI ($R^2=0.290$, $p<0.0001$; Table 3) but not PAPP-A ($p=0.933$).

The detection rates of early pre-eclampsia and late pre-eclampsia for different false positive rates in screening by maternal factors, serum PlGF, serum PAPP-A, uterine artery PI and by their combinations are given in Table 33. The performance of different methods of screening is also compared by the areas under the receiver operating characteristics curves in Table 33.

In the GH group, compared to the controls, there were no significant differences in PlGF, PAPP-A, or uterine artery PI (FIG. 1, Table 31).

The maternal serum PlGF concentration at $11^{+0}$-$13^{+6}$ weeks of gestation in normal pregnancies increased with fetal CRL and therefore gestational age, decreased with maternal weight and was higher in African American than in Caucasian women and in cigarette smokers than in non-smokers. Consequently, as in the case of PAPP-A, the measured concentration of PlGF was adjusted for these variables before comparing results with pathological pregnancies. In common with PlGF, the serum concentration of PAPP-A also increased with fetal CRL, decreased with maternal BMI and was higher in African American than in Caucasian women. However, in cigarette smokers there was an apparent dissociation in the relation between these two placental products with a decrease in serum PAPP-A and increase in PlGF.

In pregnancies developing pre-eclampsia, the maternal serum PlGF concentration at $11^{+0}$-$13^{+6}$ weeks of gestation was lower than in normotensive pregnancies. Furthermore, there was a significant association between PlGF and the severity of PE defined by both the gestation at which iatrogenic delivery was carried out and the birth weight centile of the neonates.

Thus, this example shows that PlGF, PAPP-A, and PI, and their combinations, are effective markers for detecting early pre-eclampsia and, to a lesser extent, for detecting late pre-eclampsia.

TABLE 30

Maternal characteristics in the four outcome groups

| Maternal characteristic | Control (n = 609) | Early Pre-eclampsia (n = 29) | Late Pre-eclampsia (n = 98) | Gestational hypertension (n = 88) |
|---|---|---|---|---|
| Maternal age in yrs (median, range) | 32.7 (16-45) | 32.7 (17-49) | 31.5 (18-44) | 33.3 (18-46) |
| Weight in Kg (median, range) | 65.0 (42-143) | 72.0 (54-105)* | 69.5 (44-140)† | 71.0 (50-147)‡ |
| Crown-rump length in mm (median, range) | 64.0 (45-84) | 67.0 (52-84) | 62.3 (46-84)* | 62.5 (47-83) |
| Ethnicity | | | | |
| Caucasian (n, %) | 443 (72.7) | 11 (37.9)† | 41 (41.8)‡ | 67 (76.1) |
| African American (n, %) | 97 (15.9) | 14 (48.3)‡ | 41 (41.8)‡ | 16 (18.2) |
| Indian or Pakistani (n, %) | 34 (5.6) | 2 (6.9) | 7 (7.1) | 0* |
| Chinese or Japanese (n, %) | 13 (2.1) | 0 | 2 (2.0) | 1 (1.1) |
| Mixed (n, %) | 22 (3.6) | 2 (6.9) | 7 (7.1) | 4 (4.5) |
| Parity | | | | |
| Nulliparous (n, %) | 278 (45.6) | 15 (51.7) | 64 (65.3)‡ | 49 (55.7) |
| Parous - no previous pre-eclampsia (n, %) | 315 (51.7) | 7 (24.1)* | 23 (23.5)‡ | 29 (33.0)† |
| Parous - previous pre-eclampsia (n, %) | 16 (2.6) | 7 (24.1)‡ | 11 (11.2)† | 10 (11.4)† |
| Cigarette smoker (n, %) | 30 (4.9) | 0 | 6 (6.1) | 7 (8.0) |
| Family history of pre-eclampsia - Mother (n, %) | 22 (3.6) | 3 (10.3) | 12 (12.2)† | 9 (10.2)* |
| Conception | | | | |
| Spontaneous (n, %) | 594 (97.5) | 25 (86.2)* | 94 (95.9) | 85 (96.6) |

TABLE 30-continued

Maternal characteristics in the four outcome groups

| Maternal characteristic | Control (n = 609) | Early Pre-eclampsia (n = 29) | Late Pre-eclampsia (n = 98) | Gestational hypertension (n = 88) |
|---|---|---|---|---|
| Ovulation drugs (n, %) | 10 (1.6) | 3 (10.3)* | 3 (3.1) | 0 |
| In-vitro fertilization (n, %) | 5 (0.8) | 1 (3.4) | 1 (1.0) | 3 (3.4) |
| Medical history | | | | |
| None (n, %) | 599 (98.4) | 24 (82.8)† | 93 (94.9)* | 85 (96.6) |
| Chronic hypertension (n, %) | 1 (0.2) | 4 (13.8)‡ | 4 (4.1)* | 0 |
| Diabetes mellitus (n, %) | 4 (0.7) | 0 | 0 | 2 (2.3) |
| Antiphospholipid syndrome (n, %) | 3 (0.5) | 0 | 1 (1.0) | 1 (1.1) |
| Thrombophilia (n, %) | 0 | 1 (3.4)* | 0 | 0 |
| Sickle cell disease (n, %) | 1 (0.2) | 0 | 0 | 0 |
| Human immunodeficiency viral infection (n, %) | 1 (0.2) | 0 | 0 | 0 |
| Medication during pregnancy | | | | |
| None (n, %) | 572 (93.9) | 25 (86.2) | 90 (91.8) | 76 (86.4)* |
| Anti-hypertensives (n, %) | 0 | 2 (6.9)* | 2 (2.0)* | 0 |
| Insulin (n, %) | 3 (0.5) | 0 | 0 | 2 (2.3) |
| Steroids (n, %) | 1 (0.2) | 0 | 0 | 0 |
| 13-mimetics (n, %) | 5 (0.8) | 0 | 3 (3.1) | 1 (1.1) |
| Combined asthma medications (n, %) | 6 (1.0) | 0 | 1 (1.0) | 3 (3.4) |
| Thyroxine (n, %) | 9 (1.5) | 1 (3.4) | 1 (1.0) | 2 (2.3) |
| Aspirin (n, %) | 3 (0.5) | 0 | 0 | 2 (2.3) |
| Antiepileptic (n, %) | 2 (0.3) | 0 | 0 | 1 (1.1) |
| Lithium (n, %) | 6 (1.0) | 1 (3.4) | 0 | 1 (1.1) |
| Anti-inflammatory (n, %) | 2 (0.3) | 0 | 1 (1.0) | 0 |

Comparison with unaffected group (chi square test for categorical variables and ANOVA for continuous variables):
*$P < 0.05$,
†$P < 0.01$,
‡$P < 0.0001$

TABLE 31

Median (interquartile range) of maternal serum placental growth factor PlGF) MoM, PAPP-A MoM and uterine artery pulsatility index (PI) MoM in the four outcome groups: control, early preeclampsia, late preeclampsia and gestational hypertension

| Outcome group | PlGF MoM | PAPP-A MoM | Uterine artery PI MoM |
|---|---|---|---|
| Control | 0.991 (0.799-1.286) | 1.070 (0.735-1.455) | 1.030 (0.839-1.242) |
| Early preeclampsia | 0.611 (0.480-0.839)‡ | 0.535 (0.391-0.961)‡ | 1.512 (1.204-1.653)‡ |
| Late preeclampsia | 0.822 (0.550-1.056)‡ | 0.929 (0.574-1.310)* | 1.220 (0.927-1.448)‡ |
| Gestational hypertension | 0.966 (0.712-1.246) | 0.895 (0.622-1.442) | 1.100 (0.885-1.287) |

Mann-Whitney test to compare each group with controls:
*$P < 0.05$,
†$P < 0.01$,
‡$P < 0.0001$

TABLE 32

Logistic regression analysis for the prediction of early and late preeclampsia (PE)

| Independent variable | Early preeclampsia | | | Late preeclampsia | | |
|---|---|---|---|---|---|---|
| | OR | 95% CI | P | OR | 95% CI | P |
| Log PlGF MoM | 0.01 | 0.00   0.17 | 0.002 | 0.09 | 0.03   0.32 | <0.0001 |
| Log uterine artery PI MoM | 2020561 | 5358.56   7.6E+08 | <0.0001 | 14.03 | 1.89   103.91 | 0.010 |
| Log PAPP-A MoM | 0.16 | 0.03   0.97 | 0.046 | — | — | — |
| Body mass index in Kg/m$^2$ | — | — | — | 1.11 | 1.07   1.16 | <0.0001 |
| Chronic hypertension | 237.694 | 17.33   3260.52 | <0.0001 | — | — | — |
| Black race | 3.17 | 1.17   8.56 | 0.023 | 3.92 | 2.27   6.78 | <0.0001 |

TABLE 32-continued

Logistic regression analysis for the prediction of early and late preeclampsia (PE)

| Independent variable | Early preeclampsia | | | Late preeclampsia | | |
|---|---|---|---|---|---|---|
| | OR | 95% CI | P | OR | 95% CI | P |
| Indian or Pakistani | — | — | — | 2.95 | 1.16  7.55 | 0.024 |
| Mixed race | — | — | — | 4.71 | 1.74  12.75 | 0.002 |
| Parous - no previous PE | — | — | — | 0.28 | 0.16  0.48 | <0.0001 |
| Family history of PE | — | — | — | 4.22 | 1.71  10.41 | 0.002 |

TABLE 33

Comparison of the performance of screening for pre-eclampsia by maternal factors, placental growth factor (PlGF), pregnancy associated plasma protein A (PAPP-A), uterine artery pulsatility index (PI) and by their combinations

| Screening test | Area under receiver operating curve | |
|---|---|---|
| | Early pre-eclampsia | Late pre-eclampsia |
| History, mean (95% CI) | 0.762 (0.654-0.870) | 0.788 (0.742-0.834) |
| PlGF, mean (95% CI) | 0.797 (0.705-0.888) | 0.652 (0.589-0.714) |
| PAPP-A, mean (95% CI) | 0.742 (0.639-0.846) | 0.576 0.513-0.639) |
| Uterine artery PI, mean (95% CI) | 0.826 (0.740-0.912) | 0.626 (0.560-0.692) |
| History with PlGF, mean (95% CI) | 0.881 (0.817-0.944) | 0.817 (0.775-0.859) |
| History with PAPP-A, mean (95% CI) | 0.842 (0.747-0.937) | 0.788 (0.741-0.834) |
| History with uterine artery PI, mean (95% CI) | 0.902 (0.833-0.971) | 0.801 (0.753-0.849) |
| History with PlGF and uterine artery PI, mean (95% CI) | 0.941 (0.889-0.994) | 0.817 (0.773-0.861) |
| History with PlGF, PAPP-A and uterine artery PI, mean (95% CI) | 0.936 (0.882-0.989) | — |

| | Detection rate (%) for fixed false positive rate | | | |
|---|---|---|---|---|
| | 5% | 10% | 5% | 10% |
| History, % | 39.0 | 49.0 | 29.6 | 43.9 |
| PlGF, % | 27.6 | 51.7 | 19.4 | 32.7 |
| PAPP-A, % | 24.1 | 41.4 | 8.2 | 18.4 |
| Uterine artery PI, % | 37.9 | 65.5 | 16.3 | 27.6 |
| History with PlGF, % | 55.2 | 62.1 | 28.6 | 52.0 |
| History with PAPP-A, % | 51.7 | 69.0 | 29.6 | 46.9 |
| History with uterine artery PI, % | 69.0 | 75.9 | 29.6 | 51.0 |
| History with PlGF and uterine artery PI, % | 75.9 | 89.7 | 29.6 | 49.0 |
| History with PlGF, PAPP-A and uterine artery PI, % | 75.9 | 86.2 | — | — |

Example 4

Clinical Study of the Role of Maternal Biochemical and Biophysical Markers for Detecting Chromosomal Disorders of a Fetus This example shows the usefulness of various combinations of biochemical and biophysical markers, including PlGF, PAPP-A, free beta hCG and ultrasound markers, for determining risk that a pregnant individual is carrying a fetus having a chromosomal abnormality.

Screening was performed for chromosomal abnormalities by a combination of maternal age, fetal nuchal translucency (NT) thickness and maternal serum free beta hCG and PAPP-A at $11^{+0}$-$13^{+6}$ weeks of gestation. Written informed consent was obtained from the women agreeing to participate in a research study to identify potential markers of pregnancy complications, which was approved by the King's College Hospital Ethics Committee.

Transabdominal ultrasound examination was performed to screen any major fetal defects and for measurement of fetal NT and crown-rump length (CRL). Automated machines that provide reproducible results within 30 minutes were used to measure PAPP-A and free beta hCG (DELFIA Xpress system, PerkinElmer Life and Analytical Sciences, Waltham, USA). Maternal demographic characteristics, ultrasononographic measurements and biochemical results were recorded in a computer database. Karyotype results and details on pregnancy outcomes were added into the database as soon as they became available.

The case-control study population comprised of 175 cases with fetal chromosomal abnormalities and 609 controls with no pregnancy complications resulting in the live birth of phenotypically normal neonates. The cases and controls were matched for length of storage of their biological samples.

Duplicate serum samples of 100 μl was used to measure PlGF concentration by a quantitative enzyme linked immunoassay (ELISA) technique using Quantikine® human PlGF immunoassay (R&D systems Europe Ltd., Abingdon, UK). The assays were performed on an automated ELISA processor (Dade-Behring BEP 2000, Liederbach, Germany). Absorbance readings were taken on a VICTOR$^3$ plate reader (PerkinElmer Life and Analytical Sciences, Turku, Finland) and PlGF concentrations were determined using MultiCalc software (PerkinElmer Life and Analytical Sciences, Turku, Finland). The lower limit of detection of the assay was 7 pg/mL and the between-batch imprecision was 8.3% at a PlGF concentration of 48 pg/mL, 5.6% at 342 pg/mL and 5.1% at 722 pg/mL. Samples whose coefficient of variation of the duplicates exceeded 15% were reanalyzed.

In each case and control the measured free beta hCG, PAPP-A and PlGF were converted into MoMs after adjustment for gestation, maternal age, ethnicity, weight, parity and method of conception. Box-whisker plot of PlGF MoM of cases and control was created. Mann-Whitney test was used to determine the significance of differences in the median MoM between each chromosomally abnormal group and controls. Regression analysis was then used to determine the significance of association between PlGF MoM with free beta hCG MoM and PAPP-A MoM. Similarly, the measured NT was expressed as a difference from the expected normal mean for gestation (delta value) and regression analysis was then used to determine the significance of association between PlGF MoM and delta NT.

The MOM measured value of PlGF, PAPP-A, and/or free beta hCG can be corrected for ethnicity by dividing the MOM measured value of the biochemical marker (such as PlGF, PAPP-A, or free beta hCG) by the respective median value obtained from a group of pregnant women with unaffected pregnancies of the same ethnicity of the pregnant woman. If desired, the MOM measured value of PlGF, PAPP-A, and/or free beta hCG is corrected for smoking by dividing the MOM measured value of the biochemical marker (such as PlGF, PAPP-A, or free beta hCG) by the respective median value obtained from a group of pregnant women with unaffected pregnancies who smoke.

Logistic regression analysis was used to determine if significant contributions for the detection of trisomy 21 were provided by maternal age, free beta hCG, PAPP-A and PlGF. The performance of screening was determined by receiver operating characteristic (ROC) curves. The statistical software package SPSS 15.0 (SPSS Inc., Chicago, Ill.) was used for all data analyses.

There were 90 singleton pregnancies with trisomy 21, 28 trisomy 18, 19 trisomy 13, 28 Turner syndrome and 10 triploidy. All 10 cases of triploidy had the phenotype of digynic triploidy characterized by a thin but normal looking placenta with severe asymmetrical fetal growth restriction. The maternal characteristics of cases and controls are compared in Table 35.

Figure 7:
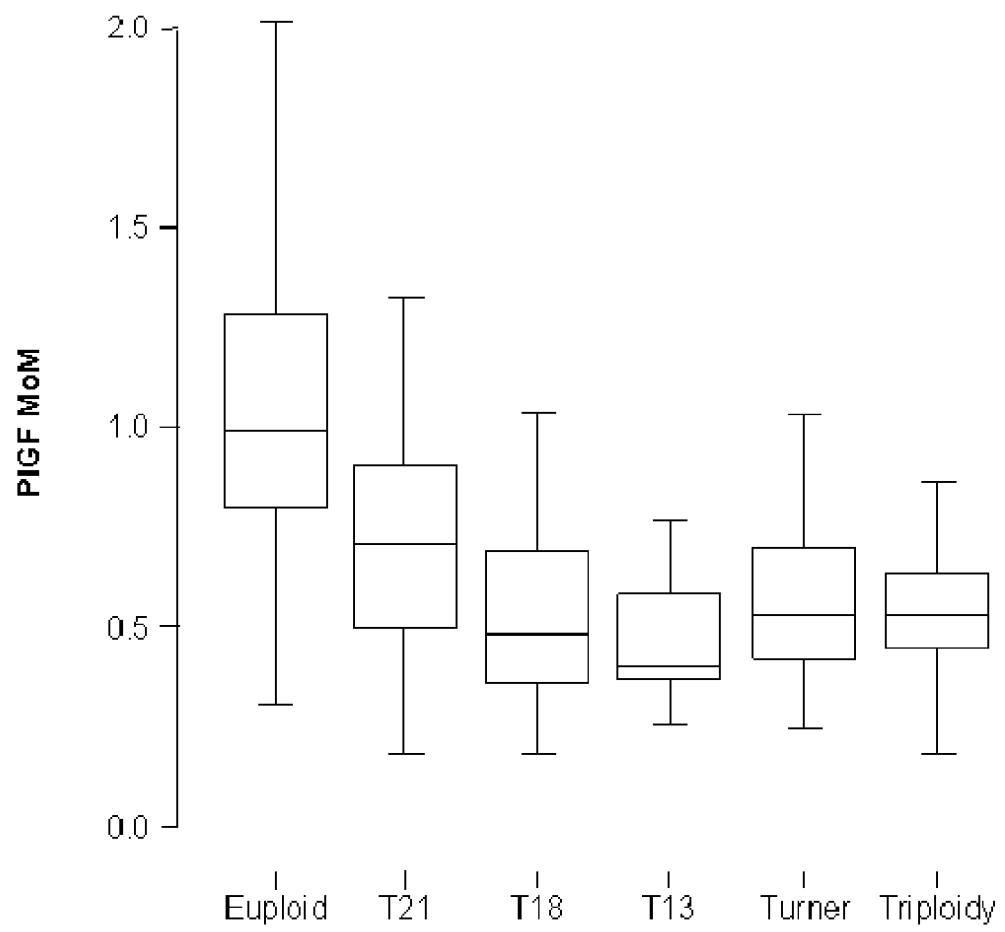
FIG. 7 is a box-whisker plot depicting a lower amount of placental growth factor (PlGF) in biological samples of pregnant individuals carrying fetuses having trisomy 21, trisomy 18, trisomy 13, Turner syndrome and triploidy, relative to unaffected fetuses.

In the euploid group, the mean log PlGF MoM was −0.004 with a standard deviation (SD) of 0.171. There was a significant association between log PlGF MoM and log PAPP-A MoM ($r=0.264$, $p<0.0001$; FIG. 7) and log free beta hCG MoM ($r=0.183$, $p<0.0001$) but not with delta NT ($p=0.054$).

Compared to the euploid group in pregnancies with trisomy 21 the median free beta hCG and fetal NT were significantly higher and PAPP-A and PlGF were significantly lower (FIG. 8, Table 37). In trisomy 21 pregnancies, the mean log PlGF MoM was −0.150 with a SD of 0.181. There was a significant association between log PlGF MoM and log PAPP-A MoM ($r=0.246$, $p=0.020$; FIG. 7), but not with log free beta hCG MoM ($p=0.652$) or delta NT ($p=0.055$). There was no significant association between log PlGF MoM with fetal CRL ($p=0.973$).

Logistic regression analysis demonstrated that significant contributions for the detection of trisomy 21 were provided from maternal age, free beta hCG, PAPP-A and PlGF ($R^2=0.662$; $p<0.0001$; Table 38). The areas under the receiver operating characteristics curves and detection rates of trisomy 21 for different false positive rates in screening by maternal age, serum PAPP-A, serum free beta hCG, serum PlGF and by their combinations are given in Table 38.

The median amounts of PlGF in trisomy 18, trisomy 13, Turner syndrome and triploidy were significantly lower than in the euploid group (FIG. 8, Table 37). The mean log PlGF MoM was −0.293 with a SD of 0.190. There was no significant association either in each individual chromosomal abnormality or in the combined group between log PlGF MoM and log PAPP-A MoM ($p=0.119$), log free beta hCG MoM ($p=0.396$) or delta NT ($p=0.701$).

The findings of this study demonstrate that firstly, in trisomy 21 as well as other major chromosomal abnormalities the maternal serum concentration of PlGF at $11^{+0}$-$13^{+6}$ weeks of gestation was decreased and secondly, measurement of PlGF can improve the performance of first-trimester biochemical screening for trisomy 21 provided by maternal serum free beta hCG and PAPP-A.

In euploid pregnancies serum PlGF increases with fetal CRL and therefore gestational age, decreases with maternal weight and is higher in African American than in Caucasian women and in cigarette smokers than in non-smokers. Consequently, as in the case of PAPP-A, the measured concentration of PlGF was adjusted for these variables before comparing results with pathological pregnancies. The results for trisomy 21 contradict those of previous smaller studies which did not adjust the measured values for maternal variables and reported that in affected pregnancies the amounts were either increased or not significantly different from normal controls.

In both the euploid and trisomy 21 pregnancies there was a significant association between serum amounts of PlGF and PAPP-A, which presumably reflects the postulated roles of these peptides in placental development and/or their common origin from cyto- and syncytio-trophoblast. However, in the trisomy 21 pregnancies there was no significant change in serum PlGF with fetal CRL indicating that the deviation between trisomic and euploid pregnancies was the same at 11 and 13 weeks. In contrast, the deviation in serum PAPP-A between trisomic and euploid pregnancies was substantially greater at 11 than at 13 weeks.

In first-trimester biochemical screening for trisomy 21 there were significant independent contributions from maternal age and serum PlGF, PAPP-A and free beta hCG. It was estimated that screening by a combination of maternal age and these three biochemical markers would identify about 70% and 80% of affected pregnancies at respective false positive rates of 3% and 5%. The amount of serum PlGF in trisomy 18, trisomy 13, Turner syndrome and triploidy is lower than in pregnancies with euploid fetuses and lower than in those with trisomy 21. It is therefore anticipated that a beneficial consequence of incorporating PlGF in first-trimester combined screening for trisomy 21 would be the detection of a high proportion of the other major aneuploidies.

TABLE 34

Studies reporting on maternal serum amounts of placental growth factor in euploid and trisomy 21 pregnancies

| Author | Gestation (wks) | Trisomy 21 | | Euploid controls | | |
|---|---|---|---|---|---|---|
| | | n | Median | n | Median | p value |
| Spencer et al 2001[4] | 10-13 | 45 | 1.26 MoM | 493 | 1.0 MoM | <0.0001 |
| Debieve et al 2001[5] | 15-20 | 24 | 0.69 MoM | 102 | 0.89 MoM | <0.001 |
| Su et al 2002[6] | 14-21 | 36 | 1.45 MoM | 320 | 1.0 MoM | <0.001 |
| Lambert-Messerlian et al 2004[7] | 15-20 | 39 | 1.01 MoM | 195 | 1.0 MoM | NS |

TABLE 35

Maternal characteristics in cases and euploid controls

| Maternal characteristic | Control (n = 609) | Trisomy 21 (n = 90) | Trisomy 18 (n = 28) | Trisomy 13 (n = 19) | Turner syndrome (n = 28) | Triploidy (n = 10) |
|---|---|---|---|---|---|---|
| Maternal age in yrs, median (range) | 32.7 (16.1-45.2) | 37.9 (19.1-46.5)‡ | 37.9 (25.3-42.6)‡ | 34.8 (29.6-44.6)† | 29.9 (18.1-37.9)* | 31.9 (20.8-37.6) |
| Maternal weight in Kg, median (range) | 65.0 (42-143) | 66.5 (42-109) | 71.4 (52-90) | 72.0 (52-85) | 66.9 (39-114) | 65.7 (50-89) |
| Crown-rump length in mm, median (range) | 64.0 (45-84) | 65 (47-84) | 57.7 (47-71)‡ | 60.1 (51-73)* | 64.6 (50-79) | 58.4 (45-74)* |
| Ethnicity | | | | | | |
| White, n (%) | 441 (72.4) | 81 (90.0)‡ | 19 (67.9) | 15 (78.9) | 26 (92.9)* | 8 (80.0) |
| Black, n (%) | 99 (16.3) | 4 (4.4)† | 4 (14.3) | 2 (10.5) | 2 (7.1) | 2 (20.) |
| Indian or Pakistani, n (%) | 4 (14.3) | 3 (3.3) | 4 (14.3) | 1 (5.3) | 0 | 0 |
| Chinese or Japanese, n (%) | 13 (2.1) | 1 (1.1) | 0 | 0 | 0 | 0 |
| Mixed, n (%) | 22 (3.6) | 1 (1.1) | 1 (3.6) | 1 (5.3) | 0 | 0 |
| Nulliparous, n (%) | 277 (45.5) | 28 (31.1)* | 12 (42.9) | 4 (21.1)* | 13 (46.4) | 7 (70.0) |
| Cigarette smoker, n (%) | 31 (5.1) | 6 (6.7) | 1 (3.6) | 1 (5.3) | 2 (7.1) | 1 (10.0) |
| Conception | | | | | | |
| Spontaneous, n (%) | 594 (97.5) | 64 (71.1)‡ | 12 (42.9)‡ | 15 (78.9)† | 18 (64.3)‡ | 8 (80.0)* |
| Ovulation drugs, n (%) | 10 (1.6) | 25 (27.8)‡ | 16 (57.1)‡ | 2 (21.1)† | 10 (35.7)‡ | 2 (20.0)* |
| In-vitro fertilization, n (%) | 5 (0.8) | 1 (1.1) | 0 | 0 | 0 | 0 |

Comparison with euploid group (chi square test for categorical variables and ANOVA for continuous variables):
*$p < 0.05$,
†$p < 0.01$,
‡$p < 0.001$

TABLE 36

Median (interquartile range) of maternal serum placental growth factor (PlGF) MoM, free beta hCG MoM, pregnancy associated plasma protein A (PAPP-A) MoM and delta nuchal translucency (NT) in euploid and chromosomally abnormal pregnancies

| Karyotype | PlGF MoM | Free beta hCG MoM | PAPP-A MoM | Delta NT in mm |
|---|---|---|---|---|
| Euploid | 0.991 (0.799-1.286) | 0.980 (0.686-1.467) | 1.070 (0.735-1.455) | 0.1 (−0.1-0.3) |
| Trisomy 21 | 0.707 (0.493-0.904)‡ | 2.530 (1.550-3.725)‡ | 0.550 (0.376-0.805)‡ | 2.2 (1.2-3.8)‡ |
| Trisomy 18 | 0.483 (0.352-0.701)‡ | 0.187 (0.142-0.300)‡ | 0.173 (0.142-0.246)‡ | 4.1 (1.0-6.0)‡ |
| Trisomy 13 | 0.404 (0.369-0.596)‡ | 0.388 (0.273-0.482)‡ | 0.252 (0.203-0.321)‡ | 2.9 (0.3-4.7)‡ |
| Turner syndrome | 0.534 (0.410-0.717)‡ | 0.965 (0.593-1.755) | 0.531 (0.409-0.820)‡ | 8.1 (6.7-10.8)‡ |
| Triploidy | 0.531 (0.437-0.668)‡ | 0.130 (0.036-0.336)‡ | 0.060 (0.041-0.080)‡ | 0.1 (−0.0-0.7) |

Comparison with euploid (Mann-Whitney test) =
*$p < 0.05$,
†$p < 0.01$,
‡$p < 0.0001$.

TABLE 37

Logistic regression analysis for the prediction of trisomy 21 by a combination of maternal age, pregnancy associated plasma protein A (PAPP-A), free beta hCG and placenta growth factor (P1GF)

| Independent variable | OR | 95% CI | | p |
|---|---|---|---|---|
| Age | 1.190 | 1.116 | 1.269 | <0.0001 |
| Log PAPP-A MoM | 0.027 | 0.006 | 0.115 | <0.0001 |
| Log beta hCG MoM | 671.150 | 150.215 | 2998.655 | <0.0001 |
| Log PlGF MoM | 0.001 | 0.000 | 0.013 | <0.0001 |

TABLE 38

Performance of maternal age, free beta hCG, pregnancy associated plasma protein A (PAPP-A) and placental growth factor (PlGF) MoM in the detection of trisomy 21

| Screening test | Areas under receiver operating characteristic curve |
|---|---|
| Maternal age, mean (95% CI) | 0.759 (0.703-0.815) |
| PlGF, mean (95% CI) | 0.775 (0.725-0.824) |
| Maternal age and PlGF, mean (95% CI) | 0.843 (0.796-0.889) |
| Free beta hCG and PAPP-A, mean (95% CI) | 0.912 (0.876-0.949) |
| Maternal age, free beta hCG and PAPP-A, mean (95% CI) | 0.926 (0.892-0.960) |
| Free beta hCG, PAPP-A, and P1GF, mean (95% CI) | 0.935 (0.905-0.964) |
| Maternal age, free beta hCG, PAPP-A, and PlGF, mean (95% CI) | 0.946 (0.918-0.973) |

| | Detection rates for fixed false positive rate (%) | |
|---|---|---|
| | 3 | 5 |
| Maternal age, % | 20.0 | 30.0 |
| PlGF, % | 22.2 | 27.8 |
| Maternal age and PlGF, % | 32.2 | 43.3 |
| Free beta hCG and PAPP-A, % | 60.0 | 67.8 |
| Maternal age, free beta hCG and PAPP-A, % | 71.1 | 76.7 |
| Free beta hCG, PAPP-A, and P1GF, % | 66.7 | 72.2 |
| Maternal age, free beta hCG, PAPP-A, and PlGF, % | 70.0 | 80.0 |

TABLE 40

MoM of PlGF, PP13, and ADAM12 for Down syndrome,
other aneuploidy, and unaffected pregnancies

| Outcome | PlGF | PP13 | ADAM12 |
|---|---|---|---|
| Down syndrome (26) | 0.56 (0.19)** | 0.88 (0.18) | 0.85 (0.17) |
| Other Aneuploidy (22) | 0.54 (0.17)*** | 0.55 (0.22)*** | 0.69 (0.11)* |
| Controls (83) | 0.94 (0.24) | 0.99 (0.19) | 1.00 (0.17) |

Significance compared with controls:
*P < 0.05;
**P < 0.0005;
***P < 0.0001

TABLE 41

| | Centiles for markers | | | | | |
|---|---|---|---|---|---|---|
| Marker | $<1^{st}$ | $<5^{th}$ | $<10^{th}$ | $>90^{th}$ | $>95^{th}$ | $>99^{th}$ |
| PlGF | 0.39 | 0.50 | 0.62 | 1.86 | 2.19 | 3.78 |
| Non-smoker | 0.40 | 0.50 | 0.62 | 1.84 | 2.15 | 3.68 |
| Smoker | 0.71 | 0.78 | 0.88 | 2.64 | 2.76 | 4.49 |
| Caucasian | 0.39 | 0.50 | 0.61 | 1.57 | 1.88 | 2.64 |
| Non-Caucasian | 0.42 | 0.54 | 0.71 | 2.33 | 2.75 | 4.51 |

TABLE 42

Detection rate using different marker combinations at
fixed false positive 10 rates, assuming parameters for
PlGF are the same throughout the 10-13 weeks window

| | DR for fixed FPR | | |
|---|---|---|---|
| Marker Combination | 1% | 3% | 5% |
| PAPP-A and free beta hCG | 33 | 49 | 58 |
| PlGF, PAPP-A, and free beta hCG | 44 | 60 | 68 |
| PAPP-A, free beta hCG, and NT | 75 | 84 | 87 |
| PLGF, PAPP-A, free beta hCG, and NT | 79 | 87 | 90 |

Other Embodiments

While the invention has been described in conjunction with the detailed description and examples thereof, the foregoing description is intended to illustrate and not limit the scope of the invention, which is defined by the scope of the appended claims. Other aspects, advantages, and modifications are within the scope of the following claims. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining the risk of a chromosomal abnormality in a fetus, comprising:
   determining the amount of placental growth factor (PlGF), pregnancy-associated plasma protein A (PAPP-A), and free human chorionic gonadotropin (free beta hCG) in one or more blood samples taken from a pregnant individual; and determining the risk of the chromosomal abnormality in the fetus using the measured amounts of PlGF, PAPP-A, and free beta hCG.

2. The method of claim 1, wherein the chromosomal abnormality is selected from the group consisting of trisomy 21, trisomy 18, trisomy 13, Turner syndrome, and triploidy.

3. The method of claim 1, further comprising determining one or more ultrasound markers of the fetus and determining the risk of the chromosomal abnormality in the fetus using the amounts of PlGF, PAPP-A, free beta hCG, and the one or more ultrasound marker of the fetus.

4. The method of claim 3, wherein the ultrasound marker is nuchal translucency.

5. The method of claim 1, further comprising determining the amount of at least one biochemical marker selected from placental protein 13 (PP13) and metalloprotease 12 (ADAM12), and determining the risk of the chromosomal abnormality in the fetus using the amounts of PlGF, PAPP-A, free beta hCG, and the at least one biochemical marker.

6. The method of claim 1, wherein the one or more blood samples are taken from the pregnant individual in the first trimester of pregnancy.

7. The method of claim 1, wherein the one or more blood samples are taken from the pregnant individual within weeks 10 to 19 of pregnancy.

8. The method of claim 1, wherein the one or more blood samples are taken from the pregnant individual within weeks 11 to 13 of pregnancy.

9. The method of claim 1, wherein the determining comprises calculating a final risk based on the prior risk of developing the chromosomal abnormality and a set of likelihood ratios based on the amounts of PlGF, PAPP-A, and free beta hCG.

10. The method of claim 9, wherein multivariate Gaussian analysis is performed to determine the likelihood ratios.

11. The method of claim 9, further comprising using likelihood ratios for one or more maternal history parameters.

12. A medical profile for a pregnant individual, comprising information for determining risk of a chromosomal abnormality in a fetus, wherein the information comprises the amounts of PlGF, PAPP-A, and free beta hCG in one or more blood samples from the pregnant individual, and wherein the medical profile is stored on a computer-readable medium.

13. The medical profile of claim 12, wherein the medical profile further comprises additional information for determining the risk of developing pre-eclampsia, wherein the additional information comprises the blood pressure of the pregnant individual.

14. An apparatus for determining risk of a chromosomal abnormality in a fetus, the apparatus comprising:
   a data input means for inputting the amounts of PlGF, PAPP-A, and free beta hCG in one or more blood samples obtained from a pregnant individual; and
   a calculation means for determining the risk of a chromosomal abnormality in a fetus using the amounts of the PlGF, PAPP-A, and free beta hCG.

15. The apparatus of claim 14, further comprising a data input means for inputting at least one of the amounts of ADAM12 and PP13 in one or more blood samples obtained from the pregnant individual; and determining the risk of a chromosomal abnormality in a fetus using the amounts of at least one of ADAM12 and PP13, and the amounts of PlGF, PAPP-A, and free beta hCG.

16. The apparatus of claim 14, wherein the apparatus further determines risk of developing pre-eclampsia, the apparatus further comprising:
   a data input means for inputting a blood pressure of the pregnant individual; and a calculation means for determining the risk of pre-eclampsia using the input amounts of one or more of PlGF and PAPP-A, and the blood pressure.

* * * * *

UNITED STATES PATENT AND TRADEMARK OFFICE
CERTIFICATE OF CORRECTION

PATENT NO. : 8,673,582 B2  
APPLICATION NO. : 13/945143  
DATED : March 18, 2014  
INVENTOR(S) : Howard Cuckle and Kypros Nicolaides Page 1 of 1

It is certified that error appears in the above-identified patent and that said Letters Patent is hereby corrected as shown below:

Title Page 2, (56) References Cited – OTHER PUBLICATIONS, Left Column, Line 35:
After "growth factor", delete "(P1GF)" and insert --(PlGF)--.

Title Page 2, (56) References Cited – OTHER PUBLICATIONS, Right Column, Line 11:
Before "concentrations in", delete "(P1GF)" and insert --(PlGF)--.

Signed and Sealed this
Twenty-fourth Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,673,582 B2
APPLICATION NO. : 13/945143
DATED : March 18, 2014
INVENTOR(S) : Howard Cuckle and Kypros Nicolaides It is certified that error appears in the above-identified patent and that said Letters Patent is hereby corrected as shown below:

Title Page 2, (56) References Cited – OTHER PUBLICATIONS, Left Column, Line 35:
After "growth factor", delete "(PIGF)" and insert --(PlGF)--.

Title Page 2, (56) References Cited – OTHER PUBLICATIONS, Right Column, Line 11:
Before "concentrations in", delete "(PIGF)" and insert --(PlGF)--.

This certificate supersedes the Certificate of Correction issued June 24, 2014.

Signed and Sealed this
Eighteenth Day of November, 2014

Michelle K. Lee
*Deputy Director of the United States Patent and Trademark Office*